United States Patent
Youn et al.

(10) Patent No.: US 9,637,511 B2
(45) Date of Patent: May 2, 2017

(54) METHOD OF FORMING THIN FILM USING A HETEROSTRUCTURED NICKEL COMPOUND

(71) Applicant: Samsung Electronics Co., Ltd., Suwon-si (KR)

(72) Inventors: Sang-chul Youn, Suwon-si (KR); Gyu-hee Park, Hwaseong-si (KR); Youn-joung Cho, Hwaseong-si (KR); Haruyoshi Sato, Tokyo (JP); Takanori Koide, Tokyo (JP); Naoki Yamada, Tokyo (JP); Akio Saito, Tokyo (JP); Akihiro Nishida, Tokyo (JP)

(73) Assignees: SAMSUNG ELECTRONICS CO., LTD., Samsung-ro, Yeongtong-gu, Suwon-si, Gyeonggi-do (KR); ADEKA CORPORATION, Higashiogu, Arakawaku, Tokyo (JP)

( * ) Notice: Subject to any disclaimer, the term of this patent is extended or adjusted under 35 U.S.C. 154(b) by 131 days.

(21) Appl. No.: 14/622,948

(22) Filed: Feb. 16, 2015

(65) Prior Publication Data

US 2015/0266913 A1    Sep. 24, 2015

(30) Foreign Application Priority Data

Mar. 19, 2014    (KR) .................. 10-2014-0032161

(51) Int. Cl.
*C23C 16/06*    (2006.01)
*C07F 15/04*    (2006.01)
(Continued)

(52) U.S. Cl.
CPC ............ *C07F 15/045* (2013.01); *C23C 16/06* (2013.01); *C23C 16/45553* (2013.01);
(Continued)

(58) Field of Classification Search
CPC .......... C23C 16/06; C23C 16/14; C23C 16/18
See application file for complete search history.

(56) References Cited

U.S. PATENT DOCUMENTS

| 4,691,077 A * | 9/1987 | Gregory ............ H01L 31/02168 136/256 |
| 6,998,178 B2 | 2/2006 | Apen et al. |

(Continued)

FOREIGN PATENT DOCUMENTS

| EP | 1041121 A1 * | 3/2000 |
| JP | 2005529983 | 10/2005 |

(Continued)

OTHER PUBLICATIONS

Li, Jiaye, et al., "On the Relative Stability of Cobalt- and Nickel-Based Amidinate Complexes Against B-Migration." International Journal of Quantum Chemistry, vol. 109, No. 4, 756-763 (2009).*

(Continued)

*Primary Examiner* — Bret Chen
(74) *Attorney, Agent, or Firm* — Muir Patent Law, PLLC

(57) ABSTRACT

A method of forming a thin film including vaporizing a nickel compound on a substrate using a heterostructured nickel compound including a nickel amidinate ligand and an aliphatic alkoxy group and providing a vapor containing the vaporized nickel compound onto the substrate, thereby forming a nickel-containing layer. Vaporizing the nickel compound on the substrate is performed in an atmosphere in which at least one selected from plasma, heat, light, and voltage is applied.

12 Claims, 14 Drawing Sheets

(51) Int. Cl.
    C23C 16/455    (2006.01)
    C23C 16/56     (2006.01)
    H01L 21/285    (2006.01)
(52) U.S. Cl.
    CPC ........ *C23C 16/56* (2013.01); *H01L 21/28518* (2013.01); *H01L 21/28556* (2013.01)

(56) References Cited

U.S. PATENT DOCUMENTS

| | | | |
|---|---|---|---|
| 7,049,005 B2 | 5/2006 | Apen et al. | |
| 7,060,204 B2 | 6/2006 | Li et al. | |
| 7,141,188 B2 | 11/2006 | Li et al. | |
| 7,205,422 B2 | 4/2007 | Norman | |
| 7,416,994 B2 | 8/2008 | Quick | |
| 7,462,732 B2 | 12/2008 | Kim et al. | |
| 7,932,347 B2 | 4/2011 | Ie et al. | |
| 8,617,305 B2* | 12/2013 | Lei | C07F 5/00 106/286.2 |
| 2001/0001436 A1* | 5/2001 | Foster | C23C 14/025 204/192.15 |
| 2005/0020702 A1 | 1/2005 | Li et al. | |
| 2008/0171890 A1 | 7/2008 | Kim et al. | |
| 2008/0254218 A1 | 10/2008 | Lei et al. | |
| 2010/0071587 A1 | 3/2010 | Byun et al. | |
| 2010/0092667 A1 | 4/2010 | Gordon et al. | |
| 2011/0104896 A1* | 5/2011 | Harada | C23C 16/0218 438/680 |
| 2011/0183527 A1 | 7/2011 | Cho et al. | |
| 2012/0168726 A1 | 7/2012 | Park et al. | |
| 2012/0168727 A1 | 7/2012 | Lee et al. | |
| 2012/0183689 A1 | 7/2012 | Suzuki et al. | |
| 2012/0201958 A1* | 8/2012 | Lei | C23C 16/45553 427/255.6 |
| 2013/0062768 A1* | 3/2013 | Waechtler | H01L 21/28562 257/750 |
| 2014/0174323 A1 | 6/2014 | Wada et al. | |
| 2014/0201958 A1* | 7/2014 | Huang | A44B 19/36 24/435 |
| 2016/0233098 A1* | 8/2016 | Nabeya | C23C 16/18 |

FOREIGN PATENT DOCUMENTS

| | | |
|---|---|---|
| JP | 2006063352 | 3/2006 |
| JP | 2008537947 | 10/2006 |
| JP | 2011-58031 A * | 3/2011 |
| JP | 4643452 | 3/2011 |
| KR | 10-2012-0079423 | 7/2012 |
| KR | 10-1216068 | 12/2012 |
| WO | WO 03/059984 A1 | 7/2003 |
| WO | WO 2006/107121 A1 | 10/2006 |
| WO | WO2013/018413 | 2/2013 |

OTHER PUBLICATIONS

Jimenez-Oses, Gonzalo, et al., "Mechanism of Alkoxy Groups Substitution by Grignard Reagents on Aromatic Rings and Experimental Verification of Theoretical Predictions of Anomalous Reactions". Journal of the American Chemical Society, 2013, 135, 6633-6642.*

Ayres, Eliane, et al., "Attachment of Inorganic Moieties Onto Aliphatic Polyurethanes". Materials Research, vol. 10, No. 2, 119-125, 2007.*

Nelkenbaum, Elza, et al., "Synthesis and Molecular Structures of Neutral Nickel Complexes." Organometallics 2005, 24, 2645-2659.*

Yang et al. "Atomic Layer Deposition of Nickel Oxide Films Using Ni ( Dmamp ) 2 and Water." Journal of Vacuum Science & Technology A 23, 1238 (2005): doi: 10.1116/1.1875172.

* cited by examiner

METHOD OF FORMING THIN FILM USING A HETEROSTRUCTURED NICKEL COMPOUND

CROSS-REFERENCE TO RELATED APPLICATIONS

This application claims priority to Korean Patent Application No. 10-2014-0032161, filed on Mar. 19, 2014, in the Korean Intellectual Property Office, the disclosure of which is incorporated herein in its entirety by reference.

BACKGROUND

The disclosure relates to a nickel (Ni) compound and a method of forming a thin film using the same, and more particularly, to a nickel alkoxide compound and a method of forming a thin film for electronic devices, the thin film using the nickel alkoxide compound.

As electronic devices have rapidly improved in terms of speed, integration, and miniaturization, an aspect ratio of patterns for forming such electronic devices has increased. Thus, a technology that provides superior gap-filling characteristics and step coverage characteristics when a nickel-containing thin film is formed in a narrow and deep space with a large aspect ratio may be useful.

SUMMARY

The present disclosure provides a nickel compound that may be used as a material compound for forming a nickel-containing layer by vaporization.

The present disclosure provides a method of forming a thin film, the method including: forming a nickel-containing layer that has a superior gap-filling and step coverage characteristics on a structure having a relatively large aspect ratio by using a nickel compound suitable that may be used as a precursor to form the nickel-containing layer by vaporization.

According to an aspect of the inventive concept, there is provided a heterostructured nickel compound including: a nickel amidinate ligand; and an aliphatic alkoxy group.

The nickel compound may be represented by the following Formula (I):

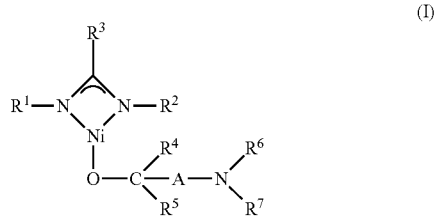

where each of R1 and R2 is a C1-C6 linear or branched alkyl group;
each of R3, R4, and R5 is hydrogen or a C1-C4 linear or branched alkyl group;
each of R6 and R7 is a C1-C4 linear or branched alkyl group; and
A is a C1-C3 alkanediyl group.

Each of R1 and R2 may be a t-butyl group, and R3 may be a methyl group.

The nickel compound represented by the Formula (I) may be a liquefied compound at room temperature.

According to another aspect of the inventive concept, there is provided a method of forming a thin film, the method including: forming a nickel-containing layer on a substrate by using a heterostructured nickel compound including a nickel amidinate ligand and an aliphatic alkoxy group.

The nickel compound may be represented by the above Formula (I).

The forming of the nickel-containing layer may include: vaporizing the nickel compound; and providing a vapor containing the vaporized nickel compound onto the substrate.

The forming of the nickel-containing layer may further include decomposing or chemically reacting the vapor containing the vaporized nickel compound on the substrate.

The vapor containing the vaporized nickel compound may further include a compound having: at least one organic coordination compound selected from an alcohol compound, a glycol compound, a β-diketone compound, a cyclopentadiene compound, and an organic amine compound; and one selected from silicon and metal.

The forming of the nickel-containing layer may include: vaporizing the nickel compound; forming a first nickel-containing layer by providing a vapor containing the vaporized nickel compound onto the substrate; and forming a second nickel-containing layer by changing a composition of the first nickel-containing layer by using at least one selected from a reactive gas and heat.

The method may further include, before the forming of the nickel-containing layer, providing the substrate in which a silicon layer is exposed, wherein the forming of the nickel-containing layer includes: forming a nickel layer on the silicon layer by using the nickel compound; and forming a nickel silicide layer from the silicon layer and the nickel layer by annealing the substrate.

The forming of the nickel-containing layer may include alternately and sequentially exposing the substrate to the nickel compound and a reactive gas. The reactive gas may be formed of a reducing gas selected from a hydrogen, an ammonia, and an organo-metallic compound.

The forming of the nickel-containing layer may be performed in an atmosphere in which at least one selected from plasma, heat, light, and voltage is applied.

The nickel-containing layer may be a nickel layer, a nickel oxide layer, a nickel nitride layer, or a nickel silicide layer.

According to an embodiment, a method of forming a thin film comprises vaporizing a nickel compound on a substrate by using a heterostructured nickel compound comprising a nickel amidinate ligand and an aliphatic alkoxy group, and providing a vapor containing the vaporized nickel compound onto the substrate, thereby forming a nickel-containing layer, wherein vaporizing the nickel compound on the substrate is performed in an atmosphere in which at least one selected from plasma, heat, light, and voltage is applied.

BRIEF DESCRIPTION OF THE DRAWINGS

Exemplary embodiments of the inventive concept will be more clearly understood from the following detailed description taken in conjunction with the accompanying drawings in which.

DETAILED DESCRIPTION OF THE EMBODIMENTS

Figure 1:
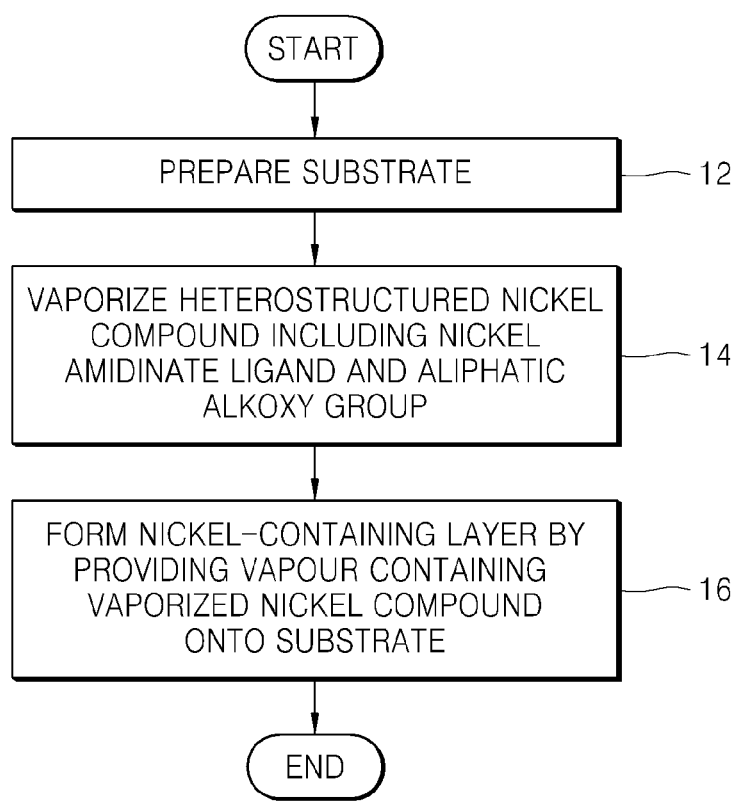
FIG. 1 is a flowchart illustrating a method of forming a thin film according to exemplary embodiments of the inventive concept.

Hereinafter, the disclosure will now be described more fully with reference to the accompanying drawings, in which exemplary embodiments of the inventive concept are shown. Like reference numerals in the drawings denote like elements, and repeated explanations of overlapped features will not be given.

The inventive concept may, however, be embodied in different forms and should not be construed as limited to the embodiments set forth herein.

It will be understood that, although the terms "first", "second", "third", etc. may be used herein to describe various elements, components, regions, layers, and/or sections, these elements, components, regions, layers, and/or sections should not be limited by these terms. Unless the context indicates otherwise, these terms are only used to distinguish one element, component, region, layer, or section from another region, layer, or section, for example as a naming convention. Thus, a first element, component, region, layer, or section discussed below could be termed a second element, component, region, layer, or section without departing from the teachings of exemplary embodiments. For example, a first element could be termed a second element, and, similarly, a second element could be termed a first element, without departing from the scope of exemplary embodiments.

Unless otherwise defined, all terms (including technical and scientific terms) used herein have the same meanings as commonly understood by one of ordinary skill in the art to which exemplary embodiments belong. It will be further understood that terms such as those defined in commonly used dictionaries should be interpreted as having meanings that are consistent with their meanings in the context of the relevant art and will not be interpreted in an idealized or overly formal sense unless expressly so defined herein.

When an exemplary embodiment may be implemented differently, a specific process order may be performed differently from the described order. For example, two consecutively described processes may be performed substantially at the same time or performed in an order opposite to the described order.

In the drawings, variations from the shapes of the illustrations as a result, for example, of manufacturing techniques and/or tolerances, are to be expected. Thus, the exemplary embodiments should not be construed as limited to the particular shapes of regions illustrated herein but may be construed to include deviations in shapes that result, for example, from manufacturing.

Unless the context indicates otherwise, terms such as "same," "equal," "planar," or "coplanar," as used herein when referring to orientation, layout, location, shapes, sizes, amounts, or other measures do not necessarily mean an exactly identical orientation, layout, location, shape, size, amount, or other measure, but are intended to encompass nearly identical orientation, layout, location, shapes, sizes, amounts, or other measures within acceptable variations that may occur, for example, due to manufacturing processes. The term "substantially" may be used herein to reflect this meaning.

As used herein, the term "and/or" includes any and all combinations of one or more of the associated listed items. Expressions such as "at least one of," when preceding a list of elements, modify the entire list of elements and do not modify the individual elements of the list.

A nickel compound according to an exemplary embodiment of the inventive concept can be a heterostructured nickel compound including a nickel amidinate ligand and an aliphatic alkoxy group.

In the present specification, the term "an akoxy group" may be expressed as —OR, where R is an alkyl group. "An alkyl group" is a substituted or unsubstituted $C_1$-$C_{20}$ linear or branched aliphatic hydrocarbon group.

The nickel compound according to the present exemplary embodiment may be represented by Formula 1:

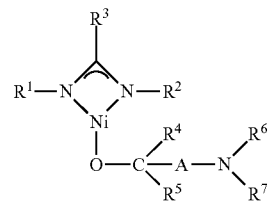

where each of $R^1$ and $R^2$ is a $C_1$-$C_6$ linear or branched alkyl group; each of $R^3$, $R^4$, and $R^5$ is hydrogen or a $C_1$-$C_4$ linear or branched alkyl group; each of $R^6$ and $R^7$ is a $C_1$-$C_4$ linear or branched alkyl group; and A is a $C_1$-$C_3$ alkanediyl group.

According to an exemplary embodiment, each of $R^1$ and $R^2$ of Formula 1 is a methyl group, a propyl group, an isopropyl group, a butyl group, an isobutyl group, a sec-butyl group, a tert-butyl group, a n-pentyl group, an amyl group, an isoamyl group, a tert-pentyl group, or a hexyl group.

According to an exemplary embodiment, each of $R^3$, $R^4$, and $R^5$ is hydrogen, a methyl group, an ethyl group, a propyl group, an isopropyl group, a butyl group, an isobutyl group, a sec-butyl group, or a tert-butyl group.

According to an exemplary embodiment, each of $R^6$ and $R^7$ is a methyl group, an ethyl group, a propyl group, an isopropyl group, a butyl group, an isobutyl group, a sec-butyl group, or a tert-butyl group.

According to an exemplary embodiment, A is a methylene group, an ethylene group, a propane-1,3-diyl group, or a propane-1,2-diyl group.

The nickel compound according to the present disclosure includes an enantiomer of the nickel compound represented by Formula 1.

In the nickel compound represented by Formula 1, $R^1$ through $R^7$ and A each may contribute to increasing an air pressure of the nickel compound, decreasing a melting point, and increasing the stability of the nickel compound, in a process of manufacturing a thin film, the process including vaporizing the nickel compound represented by Formula 1. For example, when each of $R^1$ and $R^2$ is a tert-butyl group, the stability of the nickel compound represented by Formula 1 may be increased. When $R^3$ is a methyl group, the air pressure of the nickel compound represented by Formula 1 may be increased. When each of $R^4$ and $R^5$ is a methyl group, an ethyl group, a propyl group, an isopropyl group, a butyl group, an isobutyl group, a sec-butyl group, or a tert-butyl group, the stability of the nickel compound represented by Formula 1 may be increased. When each of $R^6$ and $R^7$ is a methyl group, an ethyl group, a propyl group, an isopropyl group, a butyl group, an isobutyl group, a sec-butyl group, or a tert-butyl group, the air pressure of the nickel compound represented by Formula 1 may be increased. Also, when A is a methylene group, the air pressure of the nickel compound represented by Formula 1 may be increased.

According to an exemplary embodiment, when each of $R^1$ and $R^2$ is a tert-butyl group and $R^3$ is a methyl group, the stability of the nickel compound represented by Formula 1 is highly increased so that it becomes easy to process the nickel compound. According to another exemplary embodiment, when each of $R^1$ and $R^2$ is a tert-butyl group, $R^3$ is a methyl group, each of $R^4$ and $R^5$ is a methyl group, and each of $R^6$ and $R^7$ is a methyl group or a butyl group, a melting point of the nickel compound represented by Formula 1 may highly decrease.

If a thin film is manufactured by using a metal organic deposition (MOD) process without using a vaporization process, each of $R^1$ through $R^7$ and A may be randomly selected with respect to solubility of a solute, reaction of forming a thin film, etc.

As examples of the nickel compound according to the present disclosure, Nickel compounds 1 through 12 respectively according to Formulas 2 through 13 are illustrated. However, the nickel compound according to the present disclosure is not limited to what is illustrated according to Formulas 2 through 13. In Nickel compounds 1 through 12 respectively represented by Formulas 2 through 13, "Me" refers to a methyl group, "Et" refers to an ethyl group, "nBu" refers to a normal butyl group, and "tBu" refers to a tert-butyl group.

[Formula 2]

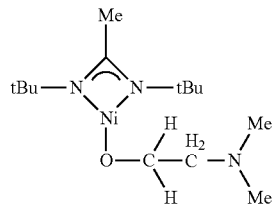

Nickel compound 1

[Formula 3]

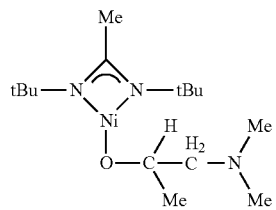

Nickel compound 2

[Formula 4]

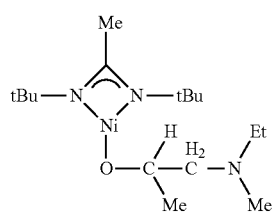

Nickel compound 3

[Formula 5]

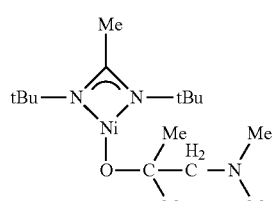

Nickel compound 4

[Formula 6]

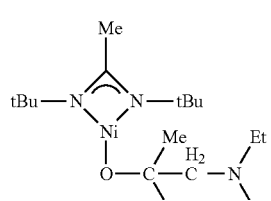

Nickel compound 5

[Formula 7]

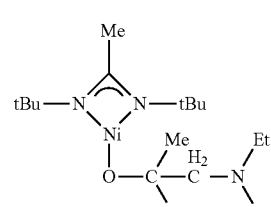

Nickel compound 6

[Formula 8]

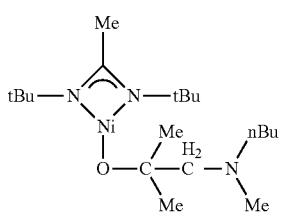

Nickel compound 7

[Formula 9]

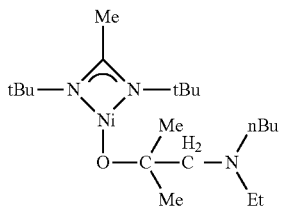

Nickel compound 8

[Formula 10]

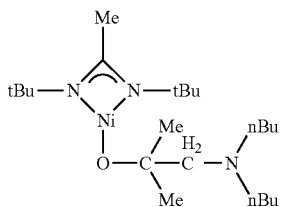

Nickel compound 9

[Formula 11]

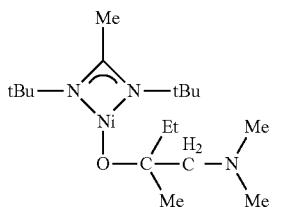

Nickel compound 10

[Formula 12]

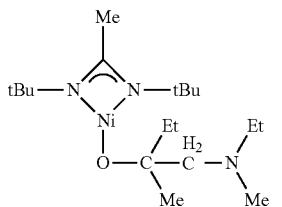

Nickel compound 11

[Formula 13]

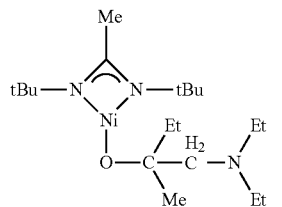

Nickel compound 12

The nickel compound according to the present disclosure has a relatively low melting point, is capable of being delivered in a liquid state, and is easily vaporized since it has a relatively high vapor pressure, and thus, may be easily delivered. Accordingly, the nickel compound is suitable to be used as a material compound to form a nickel-containing layer in a deposition process in which a material compound that is used to form a thin film is provided in a vaporized state, such as chemical vapor deposition (CVD) or atomic layer deposition (ALD). In particular, since the nickel compound according to the present disclosure has a relatively high vapor pressure, the nickel compound according to the present disclosure may be easily delivered to the structure having the relatively high aspect ratio, and thus, a nickel-containing layer having a superior gap-filling characteristic and step coverage characteristic may be formed on the structure having the relatively high aspect ratio.

The nickel compound according to the present disclosure may react with a reactive gas, for example a reducing gas such as a $H_2$ gas, at a relatively low temperature. Thus, in a process of forming a nickel-containing layer by using the nickel compound according to the present disclosure, the nickel compound does not need to be heated to a high temperature to react with the reactive gas, and thus, productivity of a process of forming a thin film may be increased.

The nickel compound according to the present disclosure may exist in a liquid state at room temperature. That is, any one selected from Nickel compounds 1 through 12 respectively represented by Formulas 2 through 13 exists in a liquid state at room temperature.

A method of manufacturing the nickel compound according to the present disclosure is not particularly limited and may be performed by using well-known reactions. For example, an amidinate compound of a desired structure may be reacted with nickel chloride to form an intermediate, and an alcohol compound of a desired structure may be reacted with the intermediate to obtain the nickel compound according to the present disclosure.

Various kinds of nickel-containing layers including a nickel element are used to manufacture electronic devices. The nickel compound according to the present disclosure may be efficiently used to form various kinds of nickel-containing layers. The nickel-containing layer obtained from the nickel compound according to the present disclosure may be used for various purposes according to electrical characteristics according to composition elements thereof. For example, the nickel-containing layer obtained from the nickel compound according to the present disclosure may be used as a wiring material that has low resistance. Also, a nickel layer obtained from the nickel compound according to the present disclosure may have excellent luster, corrosion resistance, and a strong magnetic force, and thus, the nickel layer may be used to manufacture recording media or other various devices that operate based on a magnetic force. In addition, a nickel silicide layer obtained from the nickel compound according to the present disclosure may be used as a wiring material in various kinds of electronic devices.

As semiconductor devices have become highly integrated and miniaturized, an aspect ratio of a surface of an under layer in which a nickel-containing layer is formed has increased. To form the nickel-containing layer in a narrow and deep space that has a large aspect ratio, a CVD process or an ALD process may be used. In the CVD process or the ALD process, a material compound, that is, a precursor, is vaporized and delivered to a deposition reaction chamber to form a thin film. Thus, to increase the process efficiency and productivity of the CVD or ALD process, the material compound, which has a low melting point, typically has to be delivered in a liquid state. Thus, a high vapor pressure to easily vaporize the material compound may be used.

The nickel compound according to the present disclosure has a relatively low melting point, may be delivered in a liquid state, and may be easily vaporized since it has a relatively high vapor pressure, and thus, may be easily delivered to a target site. Accordingly, the nickel compound may be used as a material compound to form a nickel-containing layer in a deposition process in which a material compound for forming a thin film is provided in a vaporized state, such as chemical vapor deposition (CVD) or atomic layer deposition (ALD). In particular, since the nickel compound according to the present disclosure has the relatively high vapor pressure, the nickel compound according to the present disclosure may be easily delivered to the structure having the relatively high aspect ratio. Thus, a nickel-containing layer having superior gap-filling characteristics and step coverage characteristics may be formed on the structure having the relatively high aspect ratio.

The nickel compound according to the present disclosure may react with a reactive gas at a relatively low temperature. Thus, in a process of forming a nickel-containing layer by using the nickel compound according to the present disclosure, the nickel compound does not need to be heated to a high temperature to react with the reactive gas, and thus, the productivity of a process of forming a thin film may be increased.

Hereinafter, a method of forming a thin film according to exemplary embodiments of the inventive concept will be described in detail.

A material compound for forming a thin film to be used in the method of forming the thin film according to the present disclosure includes the nickel compound according to the present disclosure. That is, the nickel compound according to the present disclosure is used as a precursor for forming the thin film according to the present disclosure. The nickel compound according to the present disclosure may be used in various forms according to processes of forming the thin film. The material compound for forming the thin film according to the present disclosure has a characteristic suitable to be used in the CVD process or the ALD process, and thus, it is particularly usefully applied in the CVD process or the ALD process. However, the present inventive concept is not limited thereto.

FIG. 1 is a flowchart illustrating a method of forming a thin film according to exemplary embodiments of the inventive concept.

Figure 2A:
FIGS. 2A and 2B are cross-sectional views for describing a method of forming a thin film according to exemplary embodiments of the inventive concept.
Figure 2B:
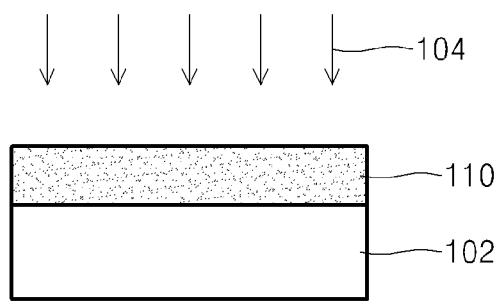

FIGS. 2A and 2B are cross-sectional views for describing a method of forming a thin film according to exemplary embodiments of the inventive concept.

Referring to FIGS. 1, 2A, and 2B, a substrate 102 is prepared in process 12.

According to an exemplary embodiment of the inventive concept, the substrate 102 may include a semiconductor element, such as silicon (Si) or germanium (Ge), or a compound semiconductor, such as silicon carbide (SiC), gallium arsenide (GaAs), indium arsenide (InAs), or indium phosphide (InP). According to another exemplary embodiment of the inventive concept, the substrate 102 may include a semiconductor substrate, and an insulating layer formed on the semiconductor substrate or structures including at least one conductive region. The conductive region may be formed of, for example, a well doped with impurities, or structures doped with impurities. Also, the substrate 102 may have various isolation structures, such as a shallow trench isolation (STI) structure.

In process 14, a heterostructured nickel compound including a nickel amidinate ligand and an aliphatic alkoxy group is vaporized.

The nickel compound may be formed as a nickel compound represented by Formula 1.

In process 16, a nickel-containing layer 110 is formed on the substrate 102 by providing a vapor 104 containing the vaporized nickel compound onto the substrate 102.

The nickel-containing layer 110 may be obtained by decomposing or chemically reacting the vapor 104 containing the vaporized nickel compound on the substrate 102.

According to an exemplary embodiment of the inventive concept, the vaporized nickel compound may be solely provided onto the substrate 102 to form the nickel-containing layer 110. According to another exemplary embodiment of the inventive concept, the vaporized nickel compound and at least one selected from another precursor, a reactive gas, a carrier gas, and a purge gas may be at the same time or sequentially provided onto the substrate 102 to form the nickel-containing layer 110. Descriptions of more detailed aspects of another precursor, the reactive gas, the carrier gas, and the purge gas that may be provided on the substrate 102 along with the vaporized nickel compound are provided later.

The nickel-containing layer 110 may be a nickel layer, a nickel oxide layer, a nickel nitride layer, a nickel silicide layer, or a combination thereof, but it is not limited thereto.

FIGS. 3A through 3D are schematic views of structures of exemplary chemical vapor deposition (CVD) devices 200A, 200B, 200C, and 200D which may be used in a process of forming a thin film according to exemplary embodiments of the inventive concept.

The CVD devices 200A, 200B, 200C, and 200D illustrated in FIGS. 3A through 3D include a fluid delivery unit 210, a thin film forming unit 250 performing a deposition process to form the thin film on a substrate W by using a process gas supplied from a material container 212 in the fluid delivery unit 210, and an exhaust system 270 to discharge a gas that is left after being used in reaction in the thin film forming unit 250 or reaction by-products.

The thin film forming unit 250 includes a reaction chamber 254 including a susceptor 252 supporting the substrate W. A shower head 256 to supply the gas supplied from the fluid delivery unit 210 onto the substrate W is formed in an upper end of the reaction chamber 254.

The fluid delivery unit 210 includes an inlet line 222 to supply a carrier gas from the outside to the material container 212 and an outlet line 224 to supply a material compound contained in the material container 212 to the thin film forming unit 250. Valves V1 and V2 and mass flow controllers (MFC) M1 and M2 may be formed in each of the inlet line 222 and the outlet line 224. The inlet line 222 and the outlet line 224 may be inter-connected via a bypass line 226. A valve V3 is formed in the bypass line 226. The valve V3 may be operated, for example, by air pressure by an electric motor or other units capable of being remotely controlled.

The material compound supplied from the material container 212 may be supplied to the reaction chamber 254 via an inlet line 266 of the thin film forming unit 250 connected to the outlet line 224 of the fluid delivery unit 210. According to necessity, the material compound supplied from the material container 212 may be supplied to the reaction chamber 254 along with the carrier gas supplied via an inlet line 268. A valve V4 and an MFC M3 may be formed in the inlet line 268 via which the carrier gas is supplied.

The thin film forming unit 250 includes an inlet line 262 to supply a purge gas into the reaction chamber 254 and an inlet line 264 to supply a reaction gas into the reaction chamber 254. Valves V5 and V6 and MFCs M4 and M5 may be formed in each of the inlet lines 262 and 264.

The process gas used in the reaction chamber 254 and the reaction by-products for disposal may be discharged to the outside by the exhaust system 270. The exhaust system 270 may include an exhaust line 272 connected with the reaction chamber 254 and a vacuum pump 274 formed in the exhaust line 272. The vacuum pump 274 may remove the process gas and the reaction by-products for disposal discharged from the reaction chamber 254.

A trap 276 may be formed in the exhaust line 272 at the upstream of the vacuum pump 274. The trap 276 may capture the reaction by-products generated from the process gas that was not completely reacted in the reaction chamber 254 so as not to make the reaction by-products flow downstream into the vacuum pump 274.

In the method of forming the thin film according to the present disclosure, the nickel compound of Formula 1 is used as the material compound to form the nickel-containing layer. In particular, the nickel compound of Formula 1 may exist in a liquid state at room temperature and be reactive to the reactive gas such as the reducing gas. Accordingly, the trap 276 formed in the exhaust line 272 may capture extraneous matter such as reaction by-products generated by a reaction between process gases to prevent the extraneous matter flowing downstream. The trap 276 may have a composition which may be cooled by a cooler or by water cooling.

Also, a bypass line 278 and an automatic pressure controller 280 may be formed in the exhaust line 272 upstream of the trap 276. Valves V7 and V8 may be respectively formed in the bypass line 278 and in a portion of the exhaust line 272, which extends in parallel to the bypass line 278.

Figure 3A:
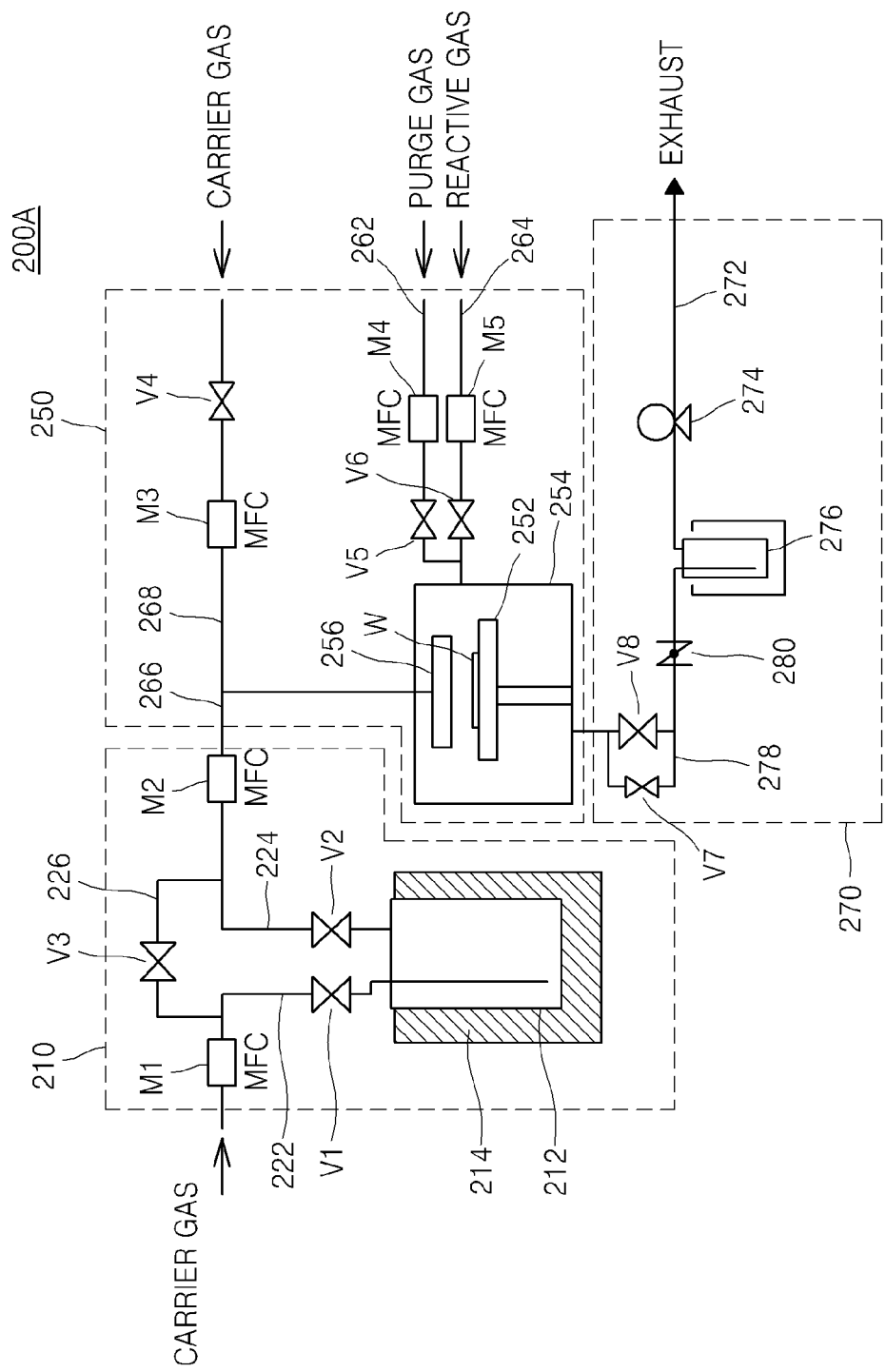
FIGS. 3A through 3D are schematic views of structures of exemplary chemical vapor deposition (CVD) devices which may be used in a process of forming a thin film according to exemplary embodiments of the inventive concept.
Figure 3B:
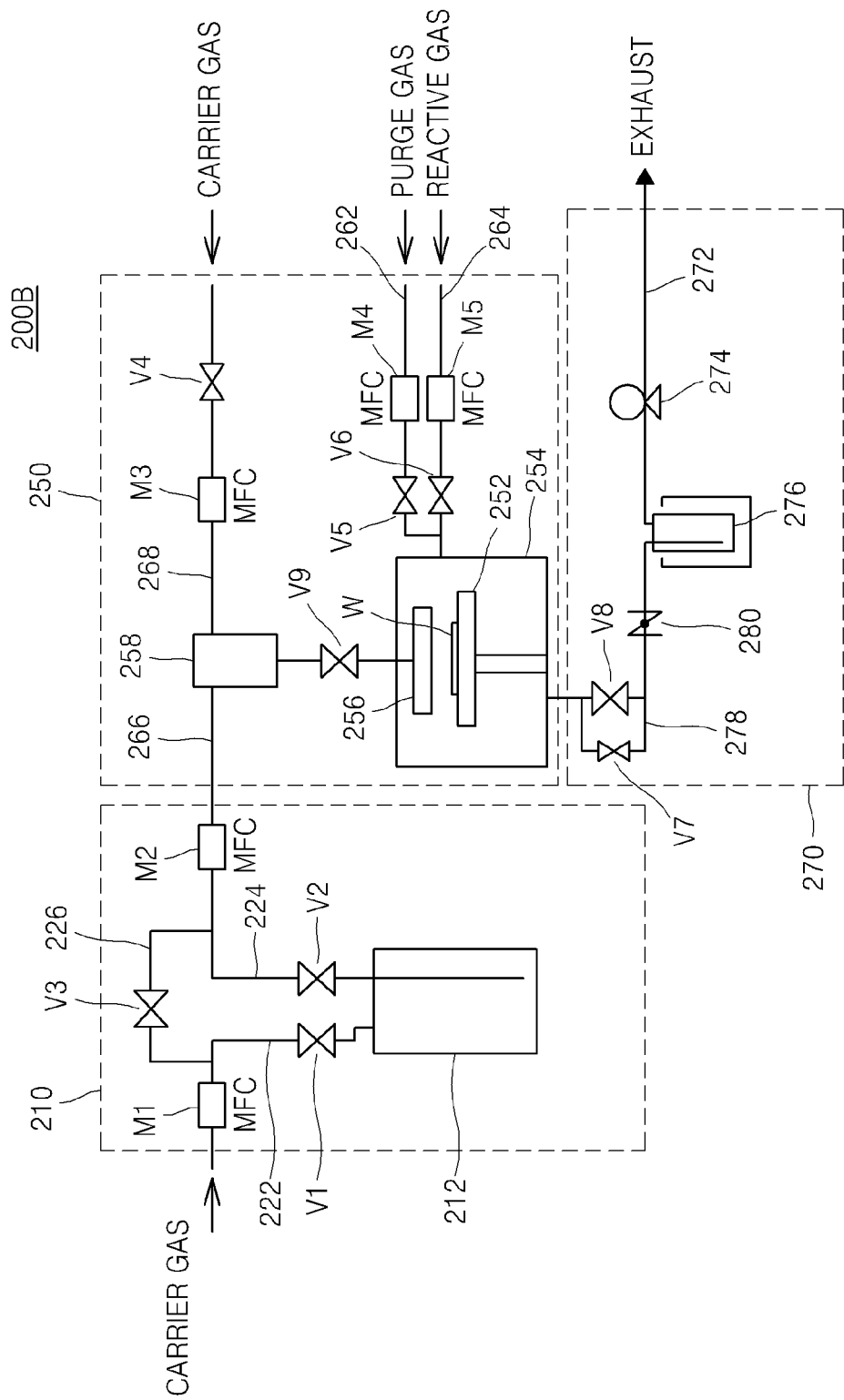
Figure 3C:
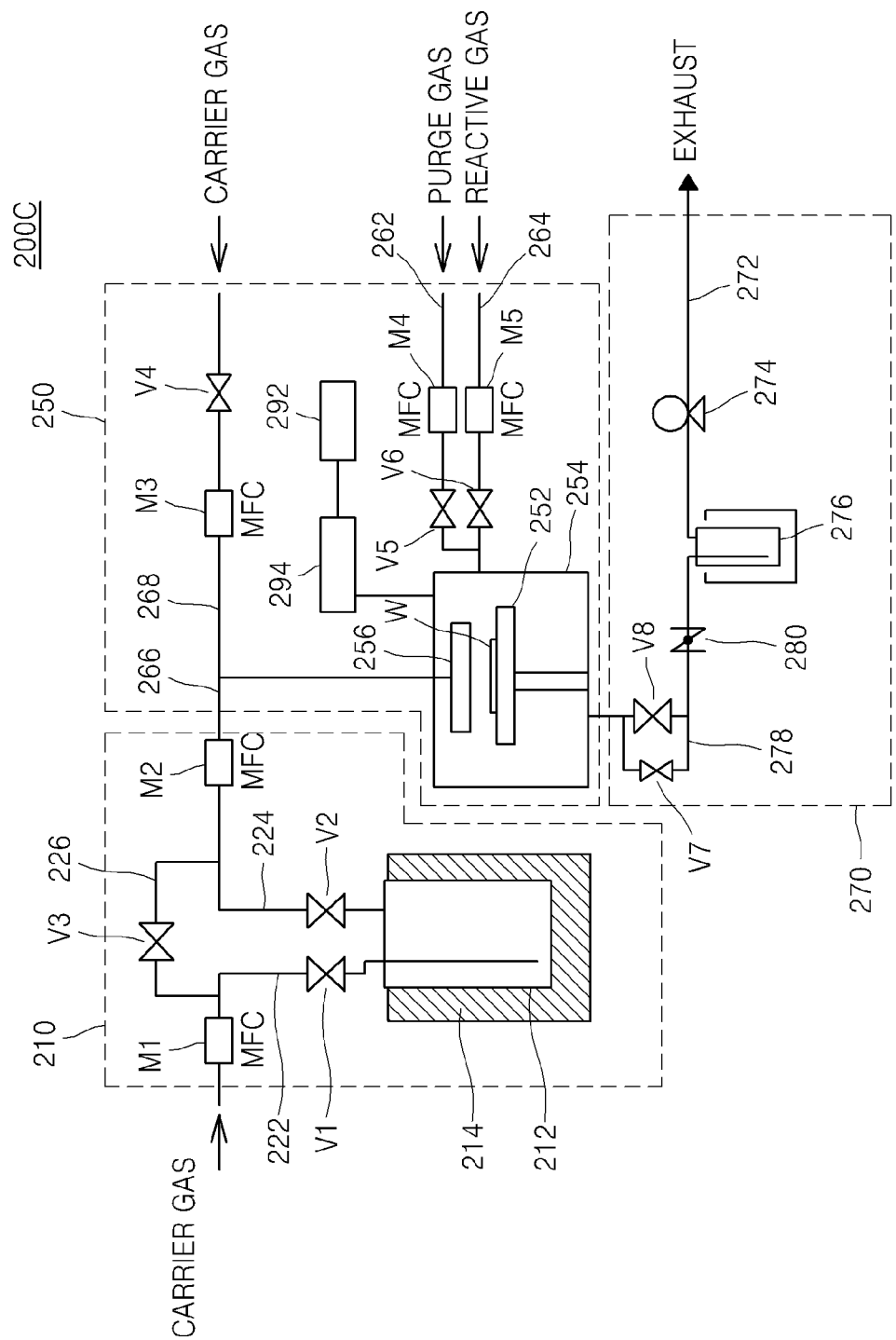

As in the CVD devices 200A and 200C illustrated in FIGS. 3A and 3C, a heater 214 may be formed in the material container 212. The temperature of the material compound contained in the material container 212 may be maintained to be relatively high by the heater 214.

Figure 3D:
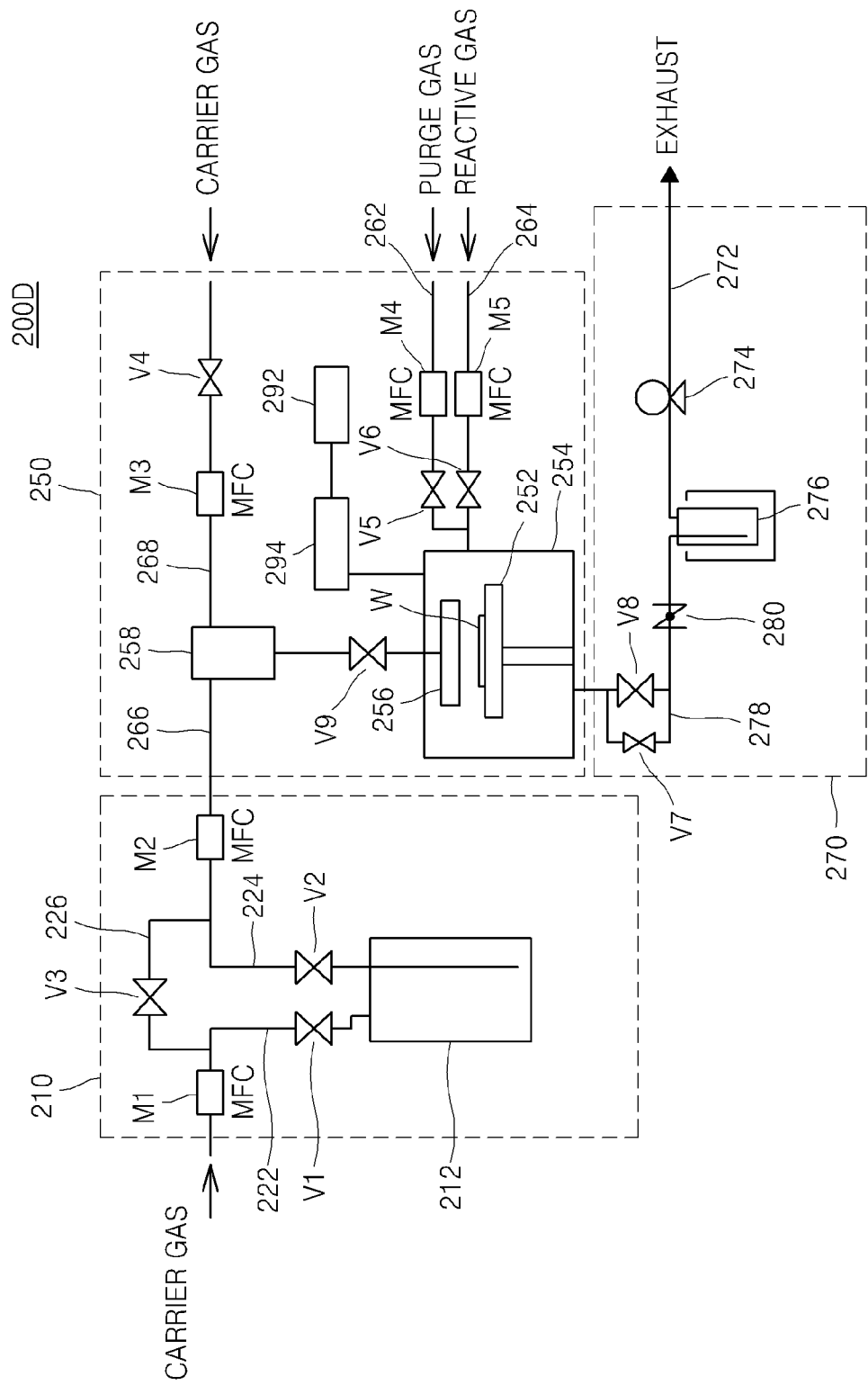

As in the CVD devices 200B and 200D illustrated in FIGS. 3B and 3D, a vaporizer 258 may be formed in the inlet line 266 of the thin film forming unit 250. The vaporizer 258 vaporizes a fluid supplied in a liquid state from the fluid delivery unit 210 and supplies the vaporized material compound into the reaction chamber 254. The material compound vaporized in the vaporizer 258 may be supplied into the reaction chamber 254 along with the carrier gas supplied via the inlet line 268. The flow of the material compound into the reaction chamber 254 through the vaporizer 258 may be controlled by a valve V9.

In addition, as in the CVD devices 200C and 200D illustrated in FIGS. 3C and 3D, the thin film forming unit 250 may include a high frequency power source 292 and an RF matching system 294 connected with the reaction chamber 254 in order to generate plasma in the reaction chamber 254.

Although it is illustrated in FIGS. 3A through 3D that the CVD devices 200A, 200B, 200C, and 200D have a structure in which one material container 212 is connected with the reaction chamber 254, it is not limited thereto. According to necessity, a plurality of material container 212 may be included in the fluid delivery unit 210, and each of the plurality of material containers 212 may be connected with the reaction chamber 254. The number of the material containers 212 connected with the reaction chamber 254 is not particularly restricted.

The vaporizer 258 may be used in any one of the CVD devices 200B and 200D illustrated in FIGS. 3B and 3D in order to vaporize the nickel compound in process 14 of FIG. 1. However, the present inventive concept is not limited thereto.

Also, any one of the CVD devices 200A, 200B, 200C, and 200D illustrated in FIGS. 3A through 3D may be used to form the nickel-containing layer 110 in process 16 of FIG. 1 and a process of FIG. 2B. However, the present inventive concept is not limited thereto.

In order to form the nickel-containing layer 110 on the substrate according to the processes of FIGS. 1, 2A, and 2B, the nickel compound may be delivered by using various methods to be supplied into a reaction chamber of a thin film forming device, for example, into the reaction chamber 254 of the CVD devices 200A, 200B, 200C, and 200D illustrated in FIGS. 3A through 3D.

According to an exemplary embodiment, in order to form a thin film by the CVD process by using the nickel compound, a gas delivery method in which the nickel compound of Formula 1 is vaporized by being heated and/or decompressed in the material container 212, and then is supplied into the reaction chamber 254 along with a carrier gas, such as Ar, $N_2$, and He, according to necessity, may be used. In the case in which the gas delivery method is used, the nickel compound of Formula 1 itself may be used as the material compound for forming the thin film in the CVD process.

According to another exemplary embodiment, in order to form the thin film by the CVD process by using the nickel compound, a liquid delivery method in which the nickel compound is delivered to the vaporizer 258 in a liquid or solution state, is vaporized by being heated and/or decompressed in the vaporizer 258, and then is supplied into the reaction chamber 254, may be used. In the case in which the liquid delivery method is used, the nickel compound itself or a solution in which the nickel compound is dissolved in an organic solvent may be used as the material compound for forming the thin film in the CVD process.

According to an exemplary embodiment, a multicomponent CVD process may be used to form the nickel-containing layer. The multicomponent CVD process may include a method in which the material compound to be used in the CVD process is vaporized separately for each component thereof and then is supplied (hereinafter, this may be referred to as a "single source method") and a method in which a mixture material that is a mixture of a desired composition of multicomponent materials is vaporized and then is supplied (hereinafter, this may be referred to as a "cocktail source method"). If the cocktail source method is used, a first mixture including the nickel compound according to the present disclosure, a first mixture solution in which the first mixture is dissolved in an organic solvent, a second mixture including the nickel compound and other precursors, or a second mixture solution in which the second mixture is dissolved in the organic solvent may be used as the material compound in a process of forming a thin film by the CVD process.

Types of the organic solvent that may be used to obtain the first mixture solution or the second mixture solution are not particularly restricted, and the organic solvents that are commonly known may be used. Examples of the organic solvents may include acetic acid esters, such as acetic acid ethyl, acetic acid butyl, and acetic acid metoxyethyl; ethers, such as tetrahydrofuran, tetrahydropyran, ethylene glycol dimethyl ether, diethylene glycol dimethyl ether, triethylene glycol dimethyl ether, dibutyl ether, and dioxane; ketones, such as methyl butyl ketone, methyl isobutyl ketone, ethyl butyl ketone, dipropyl ketone, diisobutyl ketone, methyl amyl ketone, cyclohexanone, and methylcyclohexanone;

hydrocarbons, such as hexane, cylclohexane, methylcyclohexane, dimethylcyclohexane, ethylcyclohexane, heptane, octane, toluene, and xylene; hydrocarbons having a cyano group, such as 1-cyanopropane, 1-cyanobutane, 1-cyanohexane, cyanocyclohexane, cyanobenzene, 1,3-dicyanopropane, 1,4-dicyanobutane, 1,6-dicyanohexane, 1,4-dicyanocyclohexane, and 1,4-dicyanobenzene; pyridine; and lutidine. The exemplified organic solvents may be used each independently or as a mixed solvent of at least two kinds, according to the solubility of a solute, process temperature, the boiling point, or the flash point. When these organic solvents are used, a total sum of the nickel compound of Formula 1 and other precursors in a given organic solvent may be about 0.01 to about 2.0 mol/L, for example about 0.05 to about 1.0 mol/L.

If the multicomponent CVD process is used, types of other precursors that may be used with the nickel compound according to the present disclosure are not particularly restricted, and precursors that may be used as the material compound in the CVD process may be used.

Another precursor that may be used in the method of forming the thin film according to the present disclosure may be formed as a compound of at least one organic coordination compound selected from an alcohol compound, a glycol compound, a β-diketone compound, a cyclopentadiene compound, and an organic amine compound and any one selected from silicon and metal. A metal forming the organic coordination compound may include Mg, Ca, Sr, Ba, Ti, Zr, Hf, V, Nb, Ta, Mn, Fe, Ru, Co, Rh, Ir, Pd, Pt, Cu, Ag, Au, Zn, Al, Ga, In, Ge, Sn, Pb, Sb, Bi, Y, La, Ce, Pr, Nd, Pm, Sm, Eu, Gd, Tb, Dy, Ho, Er, Tm, and Yb. However, the present inventive concept is not limited thereto.

Examples of the alcohol compound which may be used as the organic coordination compound of other precursor compounds may include alkyl alcohols, such as methanol, ethanol, propanol, isopropyl alcohol, butanol, sec-butyl alcohol, isobutyl alcohol, tert-butyl alcohol, pentyl alcohol, isopentyl alcohol, and tert-pentyl alcohol; ether alcohols, such as 2-methoxyethanol, 2-ethoxyethanol, 2-butoxyethanol, 2-(2-methoxyethoxyl)ethanol), 2-methoxy-1-dimethylethanol, 2-methoxy-1,1-dimethylethanol, 2-ethoxy-1,1-dimethylethanol, 2-isopropoxy-1,1-dimethylethanol, 2-butoxy-1,1-dimethylethanol, 2-(2-methoxyethoxy)-1,1-dimethylethanol, 2-propoxy-1,1-diethylethanol, 2-s-butoxy-1,1-diethylethanol, and 3-methoxy-1,1-dimethylpropanol; and dialkylaminoalcohol, but they are not limited thereto.

Examples of the glycol compound which may be used as the organic coordination compound of other precursor compounds may include 1,2-ethanediol, 1,2-propanediol, 1,3-propanediol, 2,4-hexanediol, 2,2-dimethyl-1,3-propanediol, 2,2-diethyl-1,3-propanediol, 1,3-butanediol, 2,4-butanediol, 2,2-diethyl-1,3-butanediol, 2-ethyl-2-butyl-1,3-propanediol, 2,4-pentanediol, 2-methyl-1,3-propanediol, 2-methyl-2,4-pentanediol, 2,4-hexanediol, and 2,4-dimethyl-2,4-pentanediol, but they are not limited thereto.

Examples of the β-diketone compound which may be used as the organic coordination compound of other precursor compounds may include alkyl-substituted β-diketones, such as acetylacetone, hexane-2,4-dione, 5-methylhexane-2,4-dione, heptane-2,4-dione, 2-methylheptane-3,5-dione, 5-methylheptane-2,4-dione, 6-methylheptane-2,4-dione, 2,2-dimethylheptane-3,5-dione, 2,6-dimethylheptane-3,5-dione, 2,2,6-trimethylheptane-3,5-dione, 2,2,6,6-tetramethylheptane-3,5-dione, octane-2,4-dione, 2,2,6-trimethyloctane-3,5-dione, 2,6-dimethyloctane-3,5-dione, 2,9-dimethylnonane-4,6-dione, 2-methyl-6-ethyldecane-3,5-dione, and 2,2-dimethyl-6-ethyldecane-3,5-dione; fluorine-substituted β-diketone, such as 1,1,1-trifluoropentane-2,4-dione, 1,1,1-trifluoro-5,5-dimethylhexane-2,4-dione, 1,1,1,5,5,5-hexafluoropentane-2,4-dione, and 1,3-diperfluorohexylpropane-1,3-dione; and ether-substituted β-diketone, such as 1,1,5,5-tetramethyl-1-methoxyhexane-2,4-dione, 2,2,6,6-tetramethyl-1-methoxyheptane-3,5-dione, and 2,2,6,6-tetramethyl-1-(2-methoxyethoxyl)heptane-3,5-dione, but they are not limited thereto.

Examples of the cyclopentadiene compound which may be used as the organic coordination compound of other precursor compound may include cyclopentadiene, methylcyclopentadiene, ethylcyclopentadiene, propylcyclopentadiene, isopropylcyclopentadiene, butylcyclopentadiene, sec-butylcyclopentadiene, isobutylcyclopentadiene, tert-butylcyclopentadiene, and dimethylcyclopentadiene, tetramethylcyclopentadiene, but they are not limited thereto.

Examples of the organic amine compound which may be used as the organic coordination compound of other precursor compounds may include methylamine, ethylamine, propylamine, isopropylamine, dimethylamine, diethylamine, dipropylamine, diisopropylamine, ethylmethylamine, propylmethylamine, and isopropylmethylamine, but they are not limited thereto.

According to a method of forming the thin film according to the exemplary embodiment illustrated in FIGS. 2A and 2B, the material compound used for forming the nickel-containing layer 110 may exist in a state not including an impurity metal element, an impurity halogen element such as impurity chlorine, and an impurity organic element until the material compound is provided onto the substrate 102.

According to an exemplary embodiment, the impurity metal element in the material compound may be included by an amount of about 100 ppb or less per one metal element, for example, about 10 ppb or less, with respect to a total amount of the material compound. Also, the total amount of the impurity metal element included in the material compound may be about 1 ppm or less, for example, about 100 ppb or less. In an embodiment, when forming a nickel-containing layer included in a gate insulating layer, a gate electrode layer, a conductive barrier layer forming a large scale integration (LSI) device, a containing amount of an alkali metal element, an alkaline-earth metal element, and an element of the same group, which affect electrical characteristics of the thin film, should be reduced as much as possible.

According to an exemplary embodiment, the impurity halogen element in the material compound may be included in an amount of about 100 ppm or less, for example, about 10 ppm or less, or about 1 ppm or less, with respect to the total amount of the material compound.

According to an exemplary embodiment, the impurity organic element in the material compound may be included by an amount of about 500 ppm or less, for example, about 50 ppm or less, or about 10 ppm or less, with respect to the total amount of the material compound.

According to an exemplary embodiment, when forming the nickel-containing layer 110 according to the method of forming the thin film according to the present disclosure, a filtering process may be performed before the material compound is introduced into the reaction chamber for forming the thin film, in order to reduce the containing amount of the impurities in the material compound Also, water in a material compound used in the CVD process may cause particles in the CVD process or the process of forming the thin film. Thus, to reduce the moisture in each of a metal compound, an organic solvent, and a nucleophilic reagent, a moisture removal process may be performed before these materials are used. A moisture amount in each of the metal compound, the organic solvent, and the nucleophilic reagent may be about 10 ppm or less, for example, about 1 ppm or less.

When forming the nickel-containing layer 110 according to the method of forming the thin film according to the present disclosure, to reduce or prevent particle contamination of the nickel-containing layer 110, an atmosphere in which the thin film is formed may be controlled not to include particles as much as possible. In detail, particle measurement by using a liquefied light-scattering-type electro particle detector may be controlled such that the number of particles larger than 0.3 μm may be 100 or less in 1 ml. According to another exemplary embodiment, the particle measurement may be controlled such that the number of particles larger than 0.2 μm may be 1000 or less in 1 ml. According to another exemplary embodiment, particle measurement may be controlled such that the number of particles larger than 0.2 μm may be 100 or less in 1 ml.

In a method of forming the thin film according to the present disclosure, the nickel-containing layer 110 may be grown and deposited on the substrate 102 by providing a vapor generated by vaporizing a mixture of the nickel compound according to the present disclosure and another precursor onto the substrate 102, along with a reactive gas if necessary, and continuously decomposing and/or reacting the precursors on the substrate 102 according to the CVD process.

In the method of forming the thin film according to the present disclosure, a method of delivering and providing the material compound, a method of deposition, a method of manufacture, a condition of manufacture, and equipment of manufacture are not particularly restricted, and general conditions and methods may be used.

Examples of the reactive gas that may be used in the method of manufacturing the semiconductor device according to the present exemplary embodiment may include an oxidative gas, a reducing gas, a nitrogen-containing gas, etc.

Examples of the oxidative gas may include oxygen, ozone, nitrogen dioxide, nitrogen monoxide, water vapor, hydrogen peroxide, formic acid, acetic acid, acetic anhydride, etc.

Examples of the reducing gas may include hydrogen, ammonia, an organo-metallic compound, etc.

Examples of the nitrogen-containing gas may include an organic amine compound, such as monoalkylamine, dialkylamine, trialkylamine, alkylenediamine, etc, hydrazine, ammonia, etc.

When forming the nickel layer in the method of forming the thin film according to the present disclosure, a compound, which has a relatively high reactivity with hydrogen which is the reducing gas, may be used as the material compound.

In the method of forming the thin film according to the present disclosure, a gas delivery method, a liquid delivery method, a single source method, or a cocktail source method may be used to provide the material compound to the reactive chamber.

In the method of forming the thin film according to the present disclosure, a heat CVD process that forms the nickel-containing layer by reacting a vaporized material compound by heat or by reacting the vaporized material compound and the reactive gas by heat, a plasma CVD process that forms a thin film by using heat and plasma, a light CVD process that uses heat and light, a light plasma CVD process that uses heat, light, and plasma, or the ALD process that performs deposition by an molecular level in stages may be used to form the nickel-containing layer. However, the present disclosure is not limited thereto.

In the method of forming the thin film according to the present disclosure, a thin film forming condition for forming the nickel-containing layer may include a reactive temperature (a substrate temperature), a reactive pressure, a deposition speed, etc.

The reactive temperature may be a temperature at which the nickel compound according to the present disclosure, for example, the nickel compound of Formula 1 may surely react, that is, about 100° C. or higher according to an exemplary embodiment, or between about 150° C. and about 300° C. according to another exemplary embodiment. However, it is not limited thereto.

The reactive pressure may be selected between an atmospheric pressure and about 10 Pa in the case of the heat CVD process or the light CVD process. The reactive pressure may be selected between about 10 Pa and about 2000 Pa in the case of the plasma CVD process. However, reactive pressure is not limited thereto.

The deposition speed may be controlled by adjusting supplying conditions (for example, a temperature of vaporization and a pressure of vaporization) of the material compound, the reactive temperature, and the reactive pressure. If the deposition speed is too high, a characteristic of a thin film consequently obtained may deteriorate, and if the deposition speed is too low, the productivity may decrease. The deposition speed of the nickel-containing layer may be about 0.01 to about 5000 nm/min, for example, the deposition speed of the nickel-containing layer may be selected between about 0.1 nm/min and about 1000 nm/min. However, it is not limited thereto. In the case in which the nickel-containing layer is formed by using the ALD process, the number of ALD cycles may be adjusted to control the nickel-containing layer to have a desired thickness.

After the forming of the nickel-containing layer 110 as described with reference to FIGS. 2A and 2B, the method of forming the thin film according to the present disclosure may further include a process of annealing under an inert atmosphere, an oxidation atmosphere, or a reducing atmosphere, in order to improve an electrical characteristic of the nickel-containing layer 110. Alternatively, a reflow process for the nickel-containing layer 110 may be performed according to necessity in order to bury a step formed on a surface of the nickel-containing layer 110. The annealing process and the reflow process may be performed at about 250 to about 1000° C., for example, the annealing process and the reflow process may be performed under a temperature condition selected between about 300° C. and about 500° C.; however they are not limited thereto.

According to the method of forming the thin film according to the present disclosure, various kinds of nickel-containing layers may be formed by appropriately selecting the material compound according to the disclosed embodiments, other precursors used along with the material compound, the reactive gas, and the thin film forming condition. According to an exemplary embodiment, the nickel-containing layer may be formed of nickel, a nickel alloy, an oxide ceramic, a nitride ceramic, or a glass. According to another exemplary embodiment, the nickel-containing layer may be formed of pure nickel, nickel oxide, nickel nitride, or nickel silicide. For example, the nickel alloy may be formed of Ni—Ti, Ni—Cr, Ni—V, Ni—Cu, Ni—Cr—Si, Ni—Cr—Al, Ni—W, AuGeNi, or $NiP_2$. The nickel oxide may be formed of NiO, $Ni_2O_3$, or $NiO_2$. The nickel nitride may be formed of nickel nitrate ($Ni(NO_3)_2$) or nickel nitrate hexahydrate ($Ni(NO_3)_2 \cdot 6H_2O$). The nickel silicide may be formed of $Ni_2Si$, $NiSi$, $NiSi_2$, or a combination thereof. However, the composition of the nickel-containing layer is not limited thereto.

The nickel-containing layer 110 manufactured according to the method of forming the thin film according to the present disclosure may be used for various usages. The nickel-containing layer may be used as a gate electrode of a transistor, an electrode of a capacitor, a conductive barrier layer for wirings, a resistive layer, a magnetic layer, a barrier metal layer for a liquid crystal display (LCD), a member for a thin film solar cell, a member for semiconductor equipment, a nano structure, a hydrogen storage alloy, a micro electro mechanical systems (MEMS) actuator, etc. However, it is not limited thereto.

Figure 4:
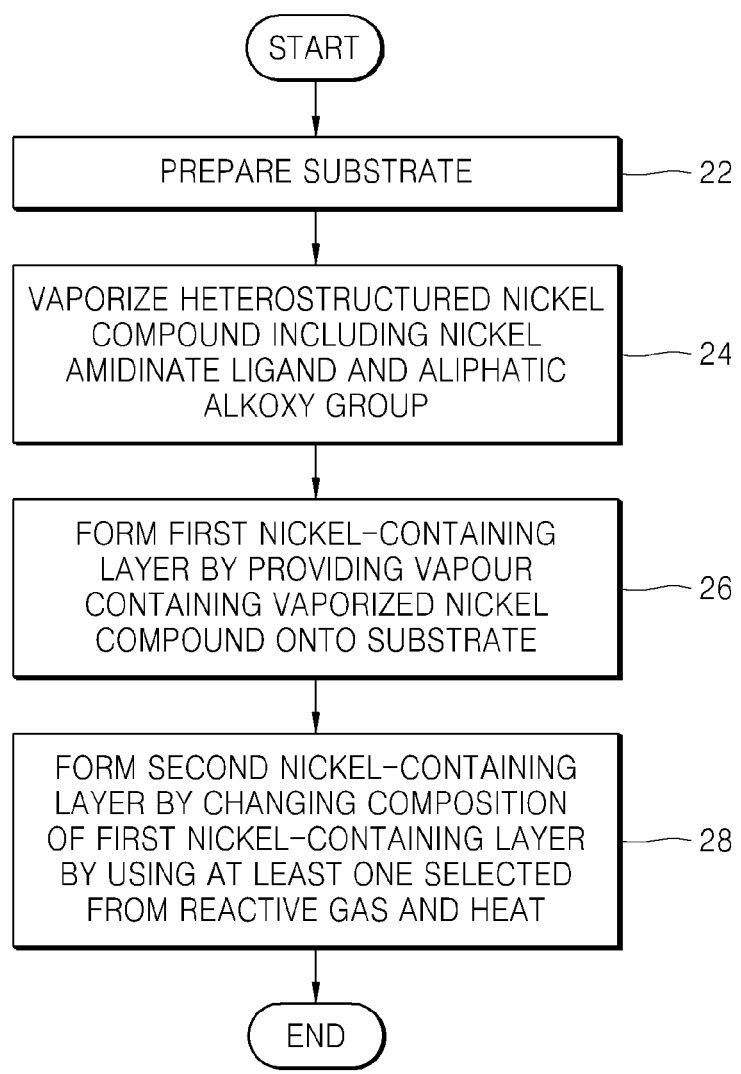
FIG. 4 is a flowchart illustrating a method of forming a thin film according to exemplary embodiments of the inventive concept.

FIG. 4 is a flowchart illustrating a method of forming a thin film according to exemplary embodiments of the inventive concept.

Figure 5A:
FIGS. 5A through 5C are cross-sectional views for describing a method of forming a thin film according to exemplary embodiments of the inventive concept.
Figure 5B:
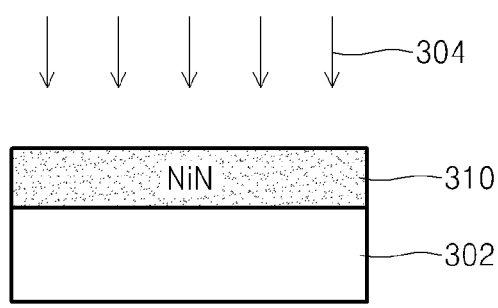
Figure 5C:
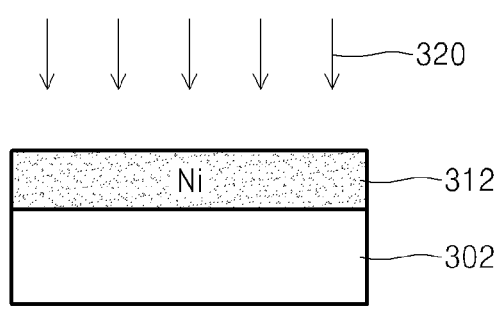

FIGS. 5A through 5C are cross-sectional views for describing a method of forming a thin film according to exemplary embodiments of the inventive concept.

Referring to FIGS. 4 and 5A through 5C, a substrate 302 is prepared in process 22. The description of the substrate 102 with reference to FIG. 2A will be referred to for more detailed aspects with respect to the substrate 302.

A heterostructured nickel compound including a nickel amidinate ligand and an aliphatic alkoxy group, is vaporized in process 24.

The nickel compound may be formed, for example, as a nickel compound represented by Formula 1.

The vaporizing process may be performed by using the vaporizer 258 included in any one of the CVD devices 200B and 200D illustrated in FIGS. 3B and 3D or a vaporizer having a similar function.

A vapor 304 containing the vaporized nickel compound is supplied onto the substrate 302 to form a first nickel-containing layer 310 on the substrate 302 in process 26.

The first nickel-containing layer 310 may be obtained by decomposing or chemically reacting the vapor 304 containing the vaporized nickel compound on the substrate 302. For example, the first nickel-containing layer 310 may be formed by the CVD process or the ALD process.

According to an exemplary embodiment, the forming of the first nickel-containing layer 310 may be performed in an atmosphere in which at least one selected from plasma, heat, light, and voltage is applied. For example, the forming of the first nickel-containing layer 310 may be performed by using any one of the CVD devices 200A, 200B, 200C, and 200D illustrated in FIGS. 3A through 3D.

According to an exemplary embodiment, the first nickel-containing layer 310 may be formed as a nickel layer including nitrogen atoms (hereinafter, this could be referred to as an "NiN layer"). The nitrogen atoms included in the first nickel-containing layer 310 may be a product obtained as nitrogen atoms included in the heterostructured nickel compound used as the material compound remain in a thin film formed on the substrate 302 during the forming of the thin film.

A second nickel-containing layer 312 is formed by changing a composition of the first nickel-containing layer 310 by using at least one of a reactive gas and heat, in process 28.

In an exemplary embodiment to form the second nickel-containing layer 312, in process 28, the second nickel-containing layer 312 formed as a nickel layer (an Ni layer) may be formed by supplying a reactive gas 320 onto the first nickel-containing layer 310 as illustrated in FIG. 5C. In an embodiment, a reducing gas, for example, a $H_2$ gas, may be used as the reactive gas 320.

In another exemplary embodiment to form the second nickel-containing layer 312, in process 28, the second nickel-containing layer 312 formed as a nickel silicide layer 314 (FIG. 7B) as described with reference to FIGS. 6, 7A and 7B may be formed.

Hereinafter, a process of forming the nickel silicide layer 314 will be described in detail by referring to FIGS. 6, 7A, and 7B.

Figure 6:
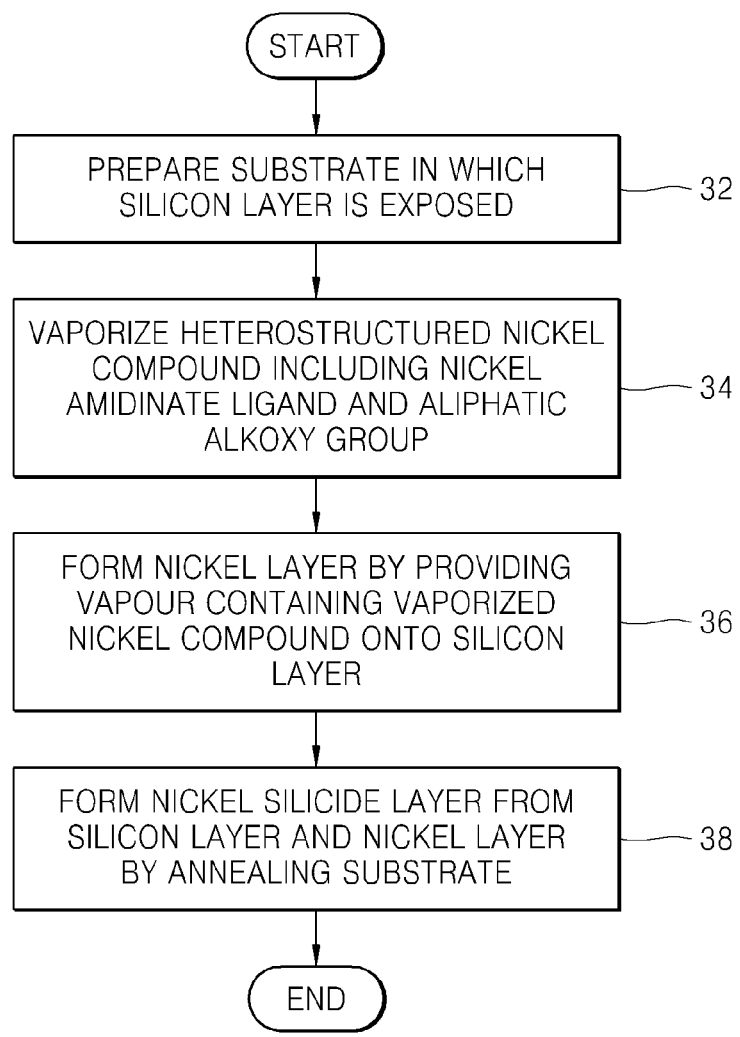
FIG. 6 is a flowchart illustrating a method of forming a thin film according to exemplary embodiments of the inventive concept.

FIG. 6 is a flowchart illustrating a method of forming a thin film according to exemplary embodiments of the inventive concept.

Figure 7A:
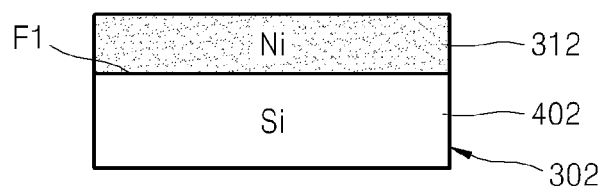
FIGS. 7A and 7B are cross-sectional views for describing a method of forming a thin film according to exemplary embodiments of the inventive concept.
Figure 7B:
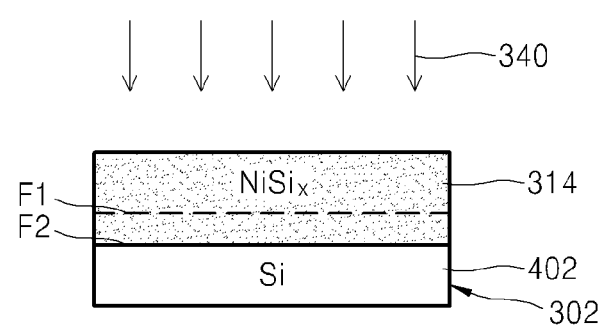

FIGS. 7A and 7B are cross-sectional views for describing a method of manufacturing a thin film according to exemplary embodiments of the inventive concept.

Referring to FIGS. 6, 7A, and 7B, the substrate 302 in which a silicon layer 402 is exposed is prepared in process 32.

For simplicity of the drawings, only the silicon layer 402 included in the substrate 302 is illustrated in FIG. 7A. However, the substrate 302 may have the same or substantially the same structure as the substrate 102 described in reference to FIG. 2A.

A heterostructured nickel compound including a nickel amidinate ligand and an aliphatic alkoxy group is vaporized in process 34, as in process 24 of FIG. 4.

The nickel compound may be formed as a nickel compound represented by Formula 1.

The vapor 304 containing the vaporized nickel compound is supplied onto the silicon layer 402 on the substrate 302 to form the nickel layer 312 as illustrated in FIG. 5C on the silicon layer 402, in process 36, as in process 26 and process 28 of FIG. 4.

The vapor 304 containing the vaporized nickel compound, and the reducing gas such as hydrogen may be supplied onto the substrate 302 at the same time to form the nickel layer 312 in process 36. Alternatively, after the first nickel-containing layer 310 formed as the NiN layer is formed by supplying the vapor 304 containing the vaporized nickel compound, the nickel layer 312 may be formed by supplying the reactive gas 320, for example, the reducing gas such as hydrogen, on the first nickel-containing layer 310, as described in reference to FIGS. 5B and 5C.

According to an exemplary embodiment, the nickel layer 312 may be formed by using the CVD process or the ALD process.

The nickel silicide ($NiSi_x$) layer 314 is formed from the silicon layer 402 and the nickel layer 312 by annealing the substrate 302 under a reducing atmosphere 340 in process 38.

According to an exemplary embodiment, a hydrogen atmosphere may be used as the reducing atmosphere 340 for annealing. The annealing may be performed at about 250° C. to about 1000° C. under the hydrogen atmosphere, for example, the annealing may be performed at a temperature condition of between about 300° C. and about 500° C. Also, the annealing may be performed for about 1 to 10 minutes, or for longer according to necessity. The annealing temperature and time may be adjusted in consideration of characteristics such as a thickness of the nickel silicide layer 314 that is to be formed and resistivity that is to be obtained in the nickel silicide layer 314.

The nickel silicide layer 314 may be formed by the reaction of the silicon layer 402 and the nickel layer 312 by the annealing. When forming the nickel silicide layer 314, a silicidation process is performed from an initial interface F1 (FIG. 7A) between the silicon layer 302 and the nickel layer 312. When the forming of the nickel silicide layer 314 is completed, a new interface F2 may be provided between the silicon layer 402 and the nickel silicide layer 314. According to an exemplary embodiment, the silicidation process may be performed with respect to substantially all of the silicon layer 402. Thus, the silicon layer 402 may not remain on the substrate 302.

After the nickel silicide layer 314 is formed, nickel of the nickel layer 312 which remains on the nickel silicide layer 314 without having participated in a silicidation process or other unnecessary materials may be removed from a surface of the nickel silicide layer 314.

The $NiSi_x$ forming the nickel silicide layer 314 may be formed of $Ni_2Si$, NiSi, $NiSi_2$, or a combination thereof.

After the nickel silicide layer 314 is formed, a phase changing process for changing from at least one phase forming the nickel silicide layer 314 to another desired phase may be additionally performed. NiSi has a relatively low resistivity compared to other nickel silicide phases. Thus, $NiSi_x$ of a phase other than NiSi may be shifted to NiSi in the phase changing process. According to an exemplary embodiment, the phase changing process and the annealing process under the reducing atmosphere 340 described in reference to FIG. 7B may be performed at the same time. According to another exemplary embodiment, the phase changing process may be performed in another reaction chamber which is different from a chamber in which the annealing process is performed. The phase changing process may be performed at a pressure of about 0.01 mbar to about 10 mbar at a temperature of about 200° C. to about 500° C. for about 5 to about 1000 seconds.

Figure 8:
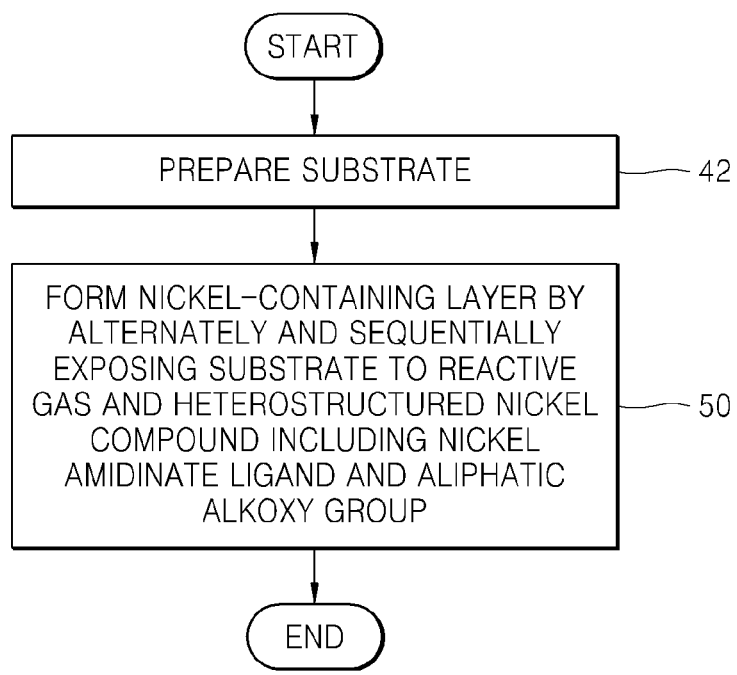
FIG. 8 is a flowchart illustrating a method of forming a thin film according to exemplary embodiments of the inventive concept.

FIG. 8 is a flowchart illustrating a method of forming a thin film according to exemplary embodiments of the inventive concept.

Referring to FIG. 8, a substrate is prepared in process 42. The substrate may be the substrate 302 described in reference to FIG. 5A.

A nickel-containing layer is formed by alternately and sequentially exposing the substrate 302 to a heterostructured nickel compound including a nickel amidinate ligand and an aliphatic alkoxy group, and a reactive gas in process 50.

The nickel compound may be the nickel compound represented by Formula 1.

The reactive gas may be a reducing gas selected from hydrogen, ammonia, and an organo-metallic compound.

An ALD process may be used to perform process 50 according to an embodiment.

Figure 9:
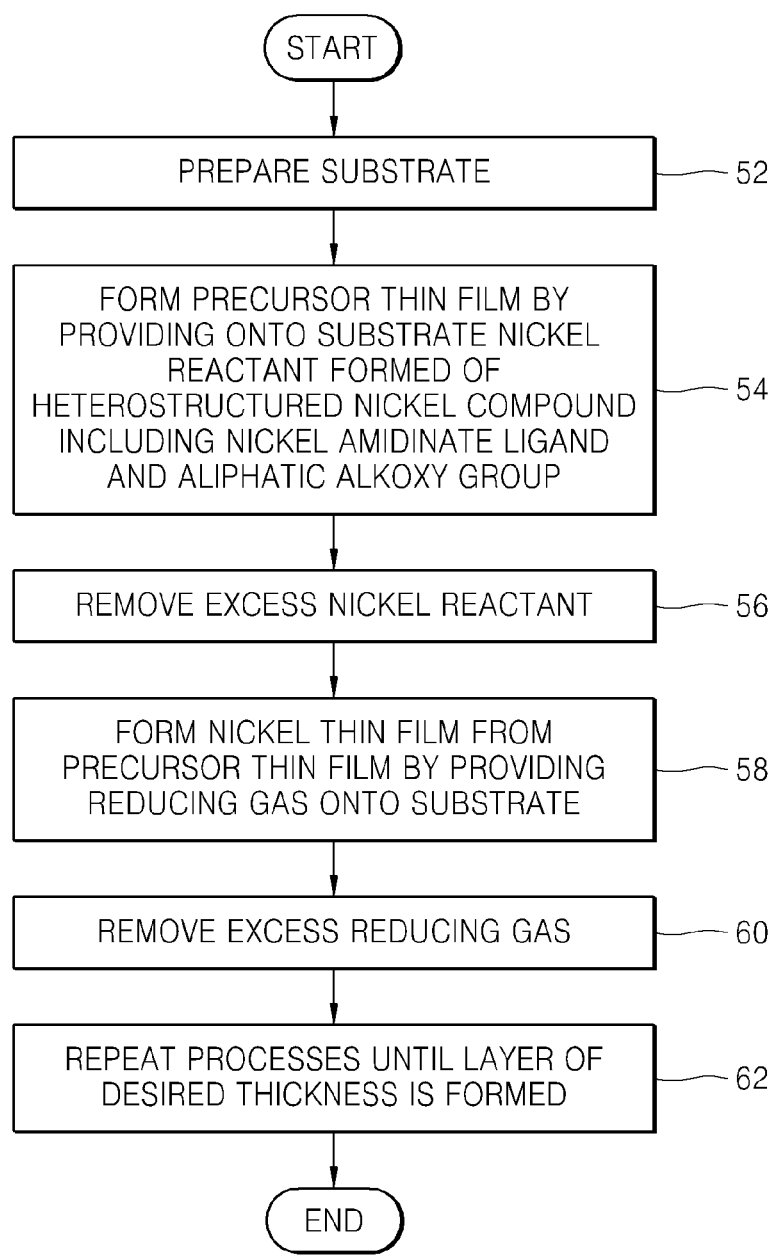
FIG. 9 is a flowchart illustrating a process of forming a Ni-containing layer by an atomic layer deposition (ALD) process in a method of forming a thin film according to exemplary embodiments of the inventive concept.

FIG. 9 is a flowchart illustrating a process of forming a Ni-containing layer by the ALD process in process 50 of FIG. 8.

Referring to FIG. 9, a substrate is prepared in process 52, and then, an Ni reactant formed of the heterostructured nickel compound including the nickel amidinate ligand and the aliphatic alkoxy group is supplied onto the substrate to perform a process of growing a precursor thin film that forms a precursor thin film on the substrate, in process 54.

The Ni reactant may be obtained from the nickel compound represented by Formula 1.

According to an exemplary embodiment, after a material compound is introduced in a deposition device for performing the ALD process, a reactant obtained from the nickel compound supplied to a deposition reaction unit is provided onto the substrate to grow the Ni precursor thin film, in order to form the nickel-containing layer by the ALD process.

Here, a process temperature may be adjusted by heating the substrate or the deposition reaction unit. The precursor thin film obtained by such a precursor thin film forming process is a nickel thin film or a thin film generated as a portion of the nickel compound is decomposed and/or reacted, and may have a different composition from a nickel thin film which is to be ultimately obtained. According to an exemplary embodiment, the process temperature of the precursor thin film forming process may be maintained at about room temperature to about 400° C., for example about 150° C. to about 300° C.

A first exhaust process that removes an excess Ni reactant from the substrate is performed in process 56.

An unreacted nickel compound gas or a reaction by-product gas may be exhausted from the deposition reaction unit in the first exhaust process. It is desirable that the unreacted nickel compound gas or the reaction by-product gas is completely exhausted from the deposition reaction unit. However, according to certain cases, it may not be completely exhausted. According to an exemplary embodiment, a purge process that uses an inert gas, such as He and Ar, may be performed for the first exhaust process. According to another exemplary embodiment, the inside of the deposition reaction unit may be decompressed. In an embodiment, a process combining the purge process and the decompressing process may be used. When the first exhaust process is performed by using the decompressing process, a decompression degree may be maintained at about 0.01 to about 50 kPa, for example about 0.1 to about 5 kPa.

A process of forming a nickel thin film that forms the nickel thin film from the precursor thin film by supplying the reducing gas onto the substrate is performed in process 58.

In the process of forming the nickel thin film, the nickel thin film is formed from the precursor thin film formed in process 54, by the reducing gas and a heat reaction.

According to an exemplary embodiment, the process of forming the nickel thin film may be performed at room temperature to about 400° C., for example at a temperature of about 150° C. to about 300° C.

The nickel compound according to the present disclosure, for example, the nickel compound represented by Formula 1 has good reactivity with the reducing gas, and thus, a desired nickel thin film may be easily obtained.

A second exhaust process that removes an excess reducing gas may be performed in process 60.

An unreacted reducing gas or a reaction by-product gas may be exhausted from the deposition reaction unit in the second exhaust process. According to an exemplary embodiment, the purge process or the decompression process may be used for the second exhaust process. The second exhaust process may be performed similarly with the first exhaust process in process 56.

Process 54 through process 60 are repeated until a layer of a desired thickness is formed in the hole, in process 62.

A thin film deposition process formed of a series of processes formed of process 54 through process 60 may be considered to be one cycle, and the cycle may be repeated a plurality of times until the layer having the desired thickness is formed. According to an exemplary embodiment, after the cycle is performed, an unreacted nickel compound gas, an unreacted reducing gas, and a reaction by-product gas may be exhausted from the deposition reaction unit by using a method similar to that of the first exhaust process in process 56 or the second exhaust process in process 60, and then, a sequential cycle may be performed.

In the forming of the nickel-containing layer by using the ALD process as described with reference to FIG. 9, energy such as plasma, light, and voltage may be applied to the deposition reaction unit while each process is performed. A period in which the energy is applied is not particularly restricted. For example, the energy may be applied when introducing raw materials into the ALD device, when introducing a nickel compound into the deposition reaction unit, when increasing the temperature in performing the process of depositing the nickel thin film according to process 54 or in performing the process of forming the nickel thin film according to process 58, when exhausting from the deposition reaction unit in the first exhaust process according to process 56 or in the second exhaust process according to process 58, when introducing the reducing gas in forming the nickel thin film according to the process 58, or between each of the aforementioned processes.

Hereinafter, exemplary embodiments of the inventive concept and evaluation embodiments will be described in detail. However, the present inventive concept is not limited to these exemplary embodiments and evaluation embodiments.

Synthesis Embodiment 1

Synthesis of Compound 5

In an argon (Ar) atmosphere, 40 g of di-tert-butylacetamidine and 160 g of dehydrated tetrahydrofuran (THF) were mixed in a reaction flask; 140 ml of a solution (1.6 mol/L) in which N-butyllithium is dissolved in hexane was dropped at −10° C.; and the solution was agitated for two hours at room temperature. Then, the solution was dropped to 14.4 g of nickel chloride and 80 g of dehydrated THF at −10° C. to be agitated for two hours at room temperature. After that, the solution was agitated for four hours at 60° C. Then, THF was removed and 150 g of hexane was added and the solution was filtered. 12 g of 1-ethylmethylamino-2-methyl-2-propanol was added to the filtered solution at room temperature to be agitated for one hour, and then agitated for two hours at 60° C. A liquid residue was obtained by removing hexane and elements having low boiling points. The liquid residue was distilled under reduced pressure and 29.1 g of desired Compound 5 were obtained by fraction at 100 Pa and a steam temperature of 100 to 101° C.

With respect to the obtained Compound 5, an element analysis, a nuclear magnetic resonance ($^1$H-NMR) analysis, and a thermogravimetry-differential thermal analysis (TG-DTA) were performed, and the results were as follows.

(1) Element Analysis (Metal Analysis: ICP-AES)

Ni: 16.2 mass % (a theoretical value 16.4 mass %), C: 57.1 mass % (a theoretical value 57.0 mass %), H: 10.3 mass % (a theoretical value 10.4 mass %), N: 11.4 mass % (a theoretical value 11.7 mass %)

(2) $^1$H-NMR (Solvent: Hexadeuterobenzene) (Chemical Shift: Multiplicity: Number of hydrogens)

CCH3 (100.0: s: 3H), NC(CH3)3 (18.04: s: 18H), EMAMP (2.92-1.10: m: 16H)

(3) TG-DTA

TG-DTA (Ar 100 ml/min, 10° C./min temperature rising, sample amount 10.02 mg)

50 mass % reduced temperature 202° C.

Synthesis Embodiment 2

Synthesis of Compound 6

In an argon (Ar) atmosphere, 40 g of di-tert-butylacetamidine and 160 g of dehydrated tetrahydrofuran (THF) were mixed in a reaction flask; 140 ml of a solution (1.6 mol/L) in which N-butyllithium is dissolved in hexane was dropped at −10° C.; and the solution was agitated for two hours at room temperature. Then, the solution was dropped to 14.4 g of nickel chloride and 80 g of dehydrated THF at −10° C. to be agitated for two hours at room temperature. After that, the solution was agitated for four hours at 60° C. Then, THF was removed and 150 g of hexane was added and the solution was filtered. 13 g of 1-diethylmethylamino-2-methyl-2-propanol was added to the filtered solution at room temperature to be agitated for one hour, and then agitated for two hours at 60° C. A liquid residue was obtained by removing hexane and elements having low boiling points. The liquid residue was distilled under reduced pressure and 30.2 g of desired Compound 6 were obtained by fraction at 100 Pa and a steam temperature of 107 to 108° C.

With respect to the obtained Compound 6, an element analysis, a nuclear magnetic resonance ($^1$H-NMR) analysis, and a thermogravimetry-differential thermal analysis (TG-DTA) were performed, and the results were as follows.

(1) Element Analysis (Metal Analysis: ICP-AES)

Ni: 15.5 mass % (a theoretical value 15.8 mass %), C: 58.0 mass % (a theoretical value 58.1 mass %), H: 10.8 mass % (a theoretical value 10.6 mass %), N: 11.2 mass % (a theoretical value 11.3 mass %)

(2) $^1$H-NMR (Solvent: Hexadeuterobenzene) (Chemical Shift: Multiplicity: Number of hydrogens)

CCH3 (99.75: s: 3H), NC(CH3)3 (17.99: s: 18H), DEAMP (3.06-1.34: m: 18H)

(3) TG-DTA

TG-DTA (Ar 100 ml/min, 10° C./min temperature rising, sample amount 9.152 mg)

50 mass % reduced temperature 210° C.

Synthesis Embodiment 3

Synthesis of Compound 7

In an argon (Ar) atmosphere, 40 g of di-tert-butylacetamidine and 160 g of dehydrated tetrahydrofuran (THF) were mixed in a reaction flask; 140 ml of a solution (1.6 mol/L) in which N-butyllithium is dissolved in hexane was dropped at −10° C.; and the solution was agitated for two hours at room temperature. The solution was dropped to 14.4 g of nickel chloride and 80 g of dehydrated THF at −10° C. to be agitated for two hours at room temperature. After that, the solution was agitated for four hours at 60° C. Then, THF was removed and 150 g of hexane was added and the solution was filtered. 14 g of 1-n-butylmethylamino-2-methyl-2-propanol was added to the filtered solution at room temperature to be agitated for one hour, and then agitated for two hours at 60° C. A liquid residue was obtained by removing hexane and elements having low boiling points. The liquid residue was distilled under reduced pressure and 31.3 g of desired Compound 7 were obtained by fraction at 100 Pa and a steam temperature of 112 to 113° C.

With respect to the obtained Compound 7, an element analysis, a nuclear magnetic resonance ($^1$H-NMR) analysis, and a thermogravimetry-differential thermal analysis (TG-DTA) were performed, and the results were as follows.

(1) Element Analysis (Metal Analysis: ICP-AES)

Ni: 15.1 mass % (a theoretical value 15.2 mass %), C: 59.3 mass % (a theoretical value 59.1 mass %), H: 10.7 mass % (a theoretical value 10.7 mass %), N: 10.6 mass % (a theoretical value 10.9 mass %)

(2) $^1$H-NMR (Solvent: Hexadeuterobenzene) (Chemical Shift: Multiplicity: Number of hydrogens)

CCH3 (99.21: s: 3H), NC(CH3)3 (17.90: s: 18H), BMAMP (3.49-1.00: m: 20H)

(3) TG-DTA

TG-DTA (Ar 100 ml/min, 10° C./min temperature rising, sample amount 10.961 mg)

50 mass % reduced temperature 214° C.

Evaluation Embodiment 1

Evaluation of a Characteristic of Ni Compound

With respect to Compounds 5, 6, and 7 respectively synthesized in embodiments 1, 2, and 3, and Comparative compounds 1, 2, and 3 respectively represented by Formulas 14, 15, and 16, states of the Compounds and Comparative compounds were observed at 30° C. at normal pressure with the naked eye. With respect to solid compounds, melting points were measured by a fine melting point measurement apparatus.

[Formula 14]

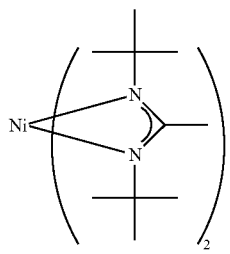

Comparative compound 1

[Formula 15]

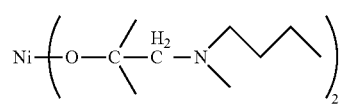

Comparative compound 2

[Formula 16]

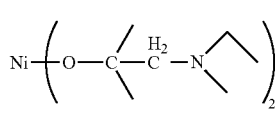

Comparative compound 3

Table 1 shows results of Evaluation embodiment 1.

TABLE 1

| | Compound | State | Melting point ° C. |
|---|---|---|---|
| Comparative embodiment 1 | Comparative compound 1 | Solid | 90 |
| Comparative embodiment 2 | Comparative compound 2 | Solid | 50 |
| Comparative embodiment 3 | Comparative compound 3 | Solid | 53 |
| Embodiment 1 | Compound 5 | Solid | 45 |
| Embodiment 2 | Compound 6 | Solid | 40 |
| Embodiment 3 | Compound 7 | Liquid | <30 |

According to Table 1, the melting points of Embodiments 1, 2, and 3 are lower than the melting points of Comparative embodiments 1, 2, and 3. Also, Compound 7 synthesized in Embodiment 3 is a compound which is a liquid under a condition of a temperature of 30° C. A material for forming a thin film, which has a low melting point, is easy to be delivered, and thus, the material may be used as a material compound for forming a thin film. This may increase the productivity of forming a nickel-containing layer.

Evaluation Embodiment 2

Evaluation of Hydrogen Reactivity of Ni Compound

With respect to Compounds 5, 6, and 7 synthesized in Embodiments 1, 2, and 3, and Comparative compounds 1 and 2, TG-DTA (hydrogen 80 ml/min, Ar 20 ml/min, 10° C./min rising temperature, sample amount about 5 mg) was measured to measure temperatures at which the compounds reacted with hydrogen. Table 2 shows the results.

TABLE 2

| | Compound | Reacting temperature (° C.) |
|---|---|---|
| Comparative embodiment 1 | Comparative compound 1 | 158 |
| Comparative embodiment 2 | Comparative compound 2 | 164 |
| Embodiment 4 | Compound 5 | 125 |
| Embodiment 5 | Compound 6 | 129 |
| Embodiment 6 | Compound 7 | 132 |

According to Table 2, the reacting temperatures of Embodiments 4, and 5, and 6 were lower than the reacting temperatures of Comparative embodiments 1 and 2. A material for forming a thin film, which reacts with a reactive gas, such as hydrogen, at a low temperature, does not need to be heated to a high temperature in a process of forming a thin film, and thus, the material increases the productivity of forming the thin film.

Thin Film Manufacture Embodiment

Manufacture of Ni Thin Film Using CVD Process

Compound 7 synthesized in Embodiment 3 was used as a material compound of the CVD process and the Ni thin film was manufactured on a silicon wafer substrate by a heat CVD process under a condition below by using the CVD device illustrated in FIG. 3A.

Material container temperature: 50° C.,
Pressure in the material container: 500 Pa,
Reacting time: 100 minutes,
Substrate temperature: 200° C.,
Carrier gas (Ar): 100 ml/min,
Reactive gas: hydrogen gas 50 ml/min, ammonia gas 200 ml/min.

A thickness of the obtained thin film was measured by X-ray reflectivity (XRR), and a structure and a composition of the obtained thin film was observed by X-ray diffraction (XRD) and X-ray photoelectron spectroscopy (XPS). As a result, the thickness of the obtained thin film was 20.0 nm, the composition of the film was Ni, and a carbon containing amount was less than 1 atom %, which is a lower limit of detection.

Figure 10:
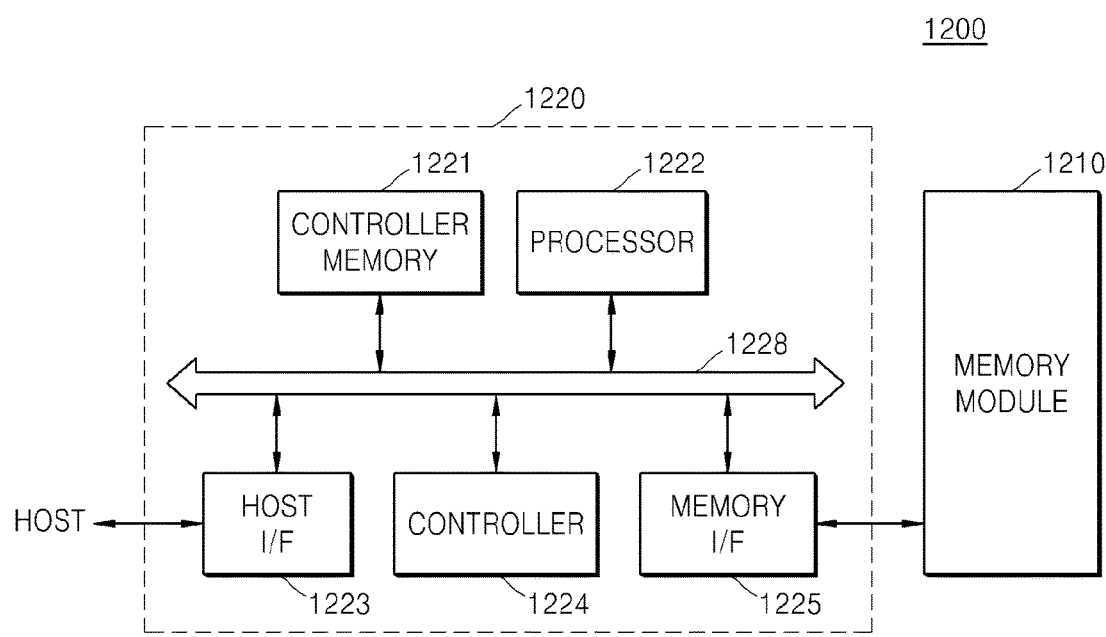
FIG. 10 is a block diagram of a memory card including an integrated circuit device manufactured according to a method of forming a thin film according to exemplary embodiments of the inventive concept.

FIG. 10 is a block diagram of a memory card 1200 including an integrated circuit device manufactured according to a method of forming a thin film according to exemplary embodiments of the inventive concept.

The memory card 1200 includes a memory controller 1220 generating a command and address signal C/A and a memory module 1210, for example a flash memory including a flash memory device or a plurality of flash memory devices. The memory controller 1220 includes a host interface 1223 transferring the command and address signal C/A to a host or receiving the command and address signal from the host and a memory interface 1225 transferring again the command and address signal C/A to the memory module 1210 or receiving the command and address signal from the memory module 1210. The host interface 1223, the controller 1224, and the memory interface 1225 communicate with a controller memory 1221 such as SRAM and a processor 1222 such as CPU via a common bus 1228.

The memory module 1210 receives the command and address signal from the memory controller 1220, stores data in at least one of memory devices in the memory module 1210 as a response, and searches the data from the at least one of the memory devices. Each memory device includes a plurality of memory cells capable of addressing and a decoder generating a row signal and a column signal to access at least one of the memory cells capable of addressing during operations of receiving the command and address signal C/A, programming, and reading.

Each of components of the memory card 1200 including the memory controller 1220, electronic devices 1221, 1222, 1223, 1224, and 1225 included in the memory controller 1220, and the memory module 1210 may include a semiconductor device including a Ni-containing layer formed according to a method of forming a thin film according to exemplary embodiments of the inventive concept.

Figure 11:
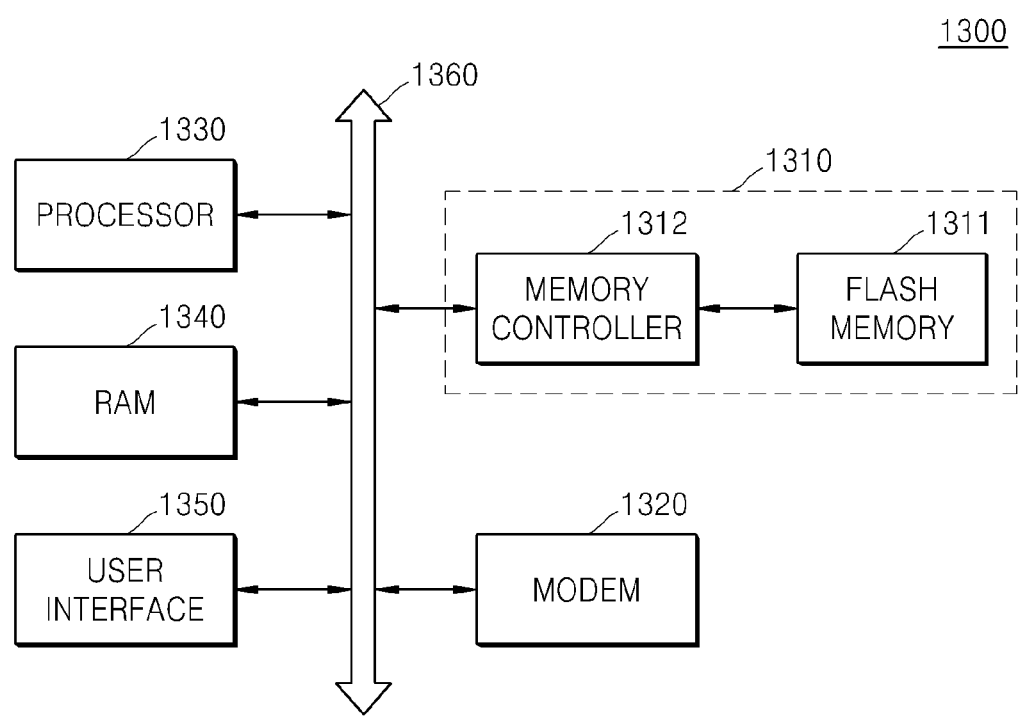
FIG. 11 is a block diagram of a memory system implementing a memory card including an integrated circuit device manufactured according to a method of forming a thin film according to exemplary embodiments of the inventive concept.

FIG. 11 is a block diagram of a memory system 1300 implementing a memory card 1310 including an integrated circuit device manufactured according to a method of forming a thin film according to exemplary embodiments of the inventive concept. The integrated circuit device may include, for example, a semiconductor device such as a semiconductor chip formed from a wafer.

The memory system 1300 may include a processor 1330 such as a CPU, random access memory 1340, a user interface 1350, and a modem 1320 that communicate with one another via a common bus 1360. Each element transfers a signal to the memory card 1310 and receives the signal from the memory card 1310 via the common bus 1360. Each of components of the memory system 1300 including the memory card 1310, the processor 1330, the random access memory 1340, the user interface 1350, and the modem 1320 may include a semiconductor device including a Ni-containing layer formed according to a method of forming a thin film according to exemplary embodiments of the inventive concept.

The memory system 1300 may be applied to various electronic applications. For example, the memory system 1300 may be applied to solid state drives (SSD), CMOS image sensors (CIS), and computer application chip sets.

The memory system 1300 and the memory devices disclosed in this specification may be packaged as a format from among various device package formats including, but not necessarily limited to, ball grid arrays (BGA), chip scale packages (CSP), plastic leaded chip carrier (PLCC), plastic dual in-line package (PDIP), multi-chip package (MCP), wafer-level fabricated package (WFP), and wafer-level processed stock package (WSP).

While the inventive concept has been particularly shown and described with reference to exemplary embodiments thereof, it will be understood that various changes in form and details may be made therein without departing from the spirit and scope of the following claims.

What is claimed is:

1. A method of forming a thin film, the method comprising:
   forming a nickel-containing layer on a substrate by vaporizing a heterostructured nickel compound comprising a nickel amidinate ligand and an aliphatic alkoxy group; and
   providing a vapor containing the vaporized nickel compound onto the substrate,
   wherein the nickel compound is represented by the following Formula (I):

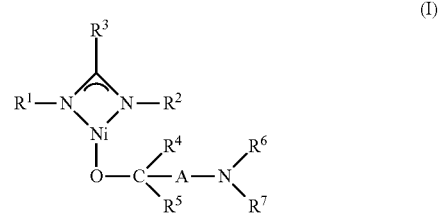

where each of $R^1$ and $R^2$ is a $C_1$-$C_6$ linear or branched alkyl group, each of $R^3$, $R^4$, and $R^5$ is hydrogen or a $C_1$-$C_4$ linear or branched alkyl group, each of $R^6$ and $R^7$ is a $C_1$-$C_4$ linear or branched alkyl group, and A is a $C_1$-$C_3$ alkanediyl group.

2. The method of claim 1, wherein the forming of the nickel-containing layer further comprises decomposing or chemically reacting the vapor containing the vaporized nickel compound.

3. The method of claim 1, wherein the vapor containing the vaporized nickel compound further comprises a compound having:
   at least one organic coordination compound selected from an alcohol compound, a glycol compound, a β-diketone compound, a cyclopentadiene compound, and an organic amine compound; and
   one selected from silicon and metal.

4. The method of claim 1, wherein the forming of the nickel-containing layer comprises:
   vaporizing the nickel compound;
   forming a first nickel-containing layer by providing a vapor containing the vaporized nickel compound onto the substrate; and
   forming a second nickel-containing layer by changing a composition of the first nickel-containing layer by using at least one selected from a reactive gas and heat.

5. The method of claim 1, further comprising, before forming the nickel-containing layer, providing the substrate in which a silicon layer is exposed,
   forming a nickel layer on the silicon layer by using the nickel compound; and
   forming a nickel silicide layer from the silicon layer and the nickel layer by annealing the substrate.

6. The method of claim 1, wherein the forming of the nickel-containing layer comprises alternately and sequentially exposing the substrate to the nickel compound and a reactive gas.

7. The method of claim 6, wherein the reactive gas comprises a reducing gas selected from hydrogen gas, ammonia gas, and an organo-metallic compound.

8. The method of claim 1, wherein the forming of the nickel-containing layer is performed in an atmosphere in which at least one selected from plasma, heat, light, and voltage is applied.

9. The method of claim 1, wherein the nickel-containing layer comprises at least one of a nickel layer, a nickel oxide layer, a nickel nitride layer, or a nickel silicide layer.

10. A method of forming a thin film, the method comprising:

forming a nickel-containing layer on a substrate using a heterostructured nickel compound comprising a nickel amidinate ligand and an aliphatic alkoxy group, wherein the nickel compound is represented by the following Formula (I):

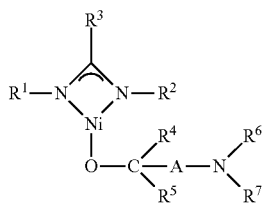

(I)

where each of $R^1$ and $R^2$ is a $C_1$-$C_6$ linear or branched alkyl group, each of $R^3$, $R^4$, and $R^5$ is hydrogen or a $C_1$-$C_4$ linear or branched alkyl group, each of $R^6$ and $R^7$ is a $C_1$-$C_4$ linear or branched alkyl group, and A is a $C_1$-$C_3$ alkanediyl group.

11. The method of claim 10, wherein the forming of the nickel-containing layer comprises:

vaporizing the nickel compound;

forming a first nickel-containing layer by providing a vapor containing the vaporized nickel compound onto the substrate; and forming a second nickel-containing layer by changing a composition of the first nickel-containing layer by using at least one selected from a reactive gas and heat.

12. The method of claim 10, further comprising, before forming the nickel-containing layer, providing the substrate in which a silicon layer is exposed, forming a nickel layer on the silicon layer by using the nickel compound; and forming a nickel silicide layer from the silicon layer and the nickel layer by annealing the substrate.

* * * * *